US010633693B1

(12) United States Patent
Handique et al.

(10) Patent No.: US 10,633,693 B1
(45) Date of Patent: Apr. 28, 2020

(54) SYSTEM AND METHOD FOR LEAKAGE CONTROL IN A PARTICLE CAPTURE SYSTEM

(71) Applicant: Celsee Diagnostics, Inc., Ann Arbor, MI (US)

(72) Inventors: Kalyan Handique, Ann Arbor, MI (US); John Stark, Ann Arbor, MI (US); Yadwinder Deol, Ann Arbor, MI (US); Vishal Sharma, Ann Arbor, MI (US)

(73) Assignee: Celsee Diagnostics, Inc., Ann Arbor, MI (US)

( * ) Notice: Subject to any disclaimer, the term of this patent is extended or adjusted under 35 U.S.C. 154(b) by 0 days.

(21) Appl. No.: 16/564,375

(22) Filed: Sep. 9, 2019

Related U.S. Application Data

(60) Provisional application No. 62/834,824, filed on Apr. 16, 2019.

(51) Int. Cl.
| | | |
|---|---|---|
| *C12Q 1/6811* | (2018.01) | |
| *C12Q 1/6874* | (2018.01) | |
| *C12N 15/10* | (2006.01) | |

(52) U.S. Cl.
CPC ........ *C12Q 1/6811* (2013.01); *C12N 15/1065* (2013.01); *C12Q 1/6874* (2013.01); *C12Q 2563/179* (2013.01); *C12Q 2565/629* (2013.01); *C12Q 2600/178* (2013.01)

(58) Field of Classification Search
CPC .......................... C12Q 1/6811; C12N 15/1065
See application file for complete search history.

(56) References Cited

U.S. PATENT DOCUMENTS

| | | | |
|---|---|---|---|
| 7,588,672 B2 | 9/2009 | Unger et al. | |
| 8,628,923 B2 | 1/2014 | Hamilton et al. | |
| 8,802,367 B2 | 8/2014 | Taniguchi et al. | |
| 9,194,001 B2 | 11/2015 | Brenner | |
| 9,249,459 B2 | 2/2016 | Hamilton et al. | |
| 9,260,753 B2 | 2/2016 | Xie et al. | |
| 9,290,808 B2 | 3/2016 | Fodor et al. | |
| 9,290,809 B2 | 3/2016 | Fodor et al. | |
| 9,304,065 B2 | 4/2016 | Fowler et al. | |
| 9,315,857 B2 | 4/2016 | Fu et al. | |
| 9,329,170 B2 | 5/2016 | Clarke et al. | |
| 9,364,829 B2 | 6/2016 | Heid et al. | |
| 9,410,201 B2 | 8/2016 | Hindson et al. | |
| 9,429,500 B2 | 8/2016 | Fowler et al. | |
| 9,506,845 B2 | 11/2016 | Fowler et al. | |
| 9,567,645 B2 | 2/2017 | Fan et al. | |
| 9,567,646 B2 | 2/2017 | Fan et al. | |
| 9,598,736 B2 | 3/2017 | Fan et al. | |
| 9,637,799 B2 | 5/2017 | Fan et al. | |
| 9,701,998 B2 | 7/2017 | Hindson et al. | |
| 9,708,659 B2 | 7/2017 | Fodor et al. | |
| 9,757,707 B2 | 9/2017 | Husain et al. | |
| 9,840,732 B2 | 12/2017 | Anderson et al. | |
| 9,845,502 B2 | 12/2017 | Fodor et al. | |
| 9,850,483 B2 | 12/2017 | Clarke et al. | |
| 9,952,126 B2 | 4/2018 | Fowler et al. | |
| 9,995,662 B2 | 6/2018 | Husain et al. | |
| 2009/0258383 A1 | 10/2009 | Kovac et al. | |
| 2014/0212881 A1* | 7/2014 | Handique | C12Q 1/686 435/6.12 |
| 2015/0133319 A1 | 5/2015 | Fu et al. | |
| 2015/0204864 A1 | 7/2015 | Fan et al. | |
| 2015/0299784 A1* | 10/2015 | Fan | C12Q 1/6874 506/4 |
| 2015/0376609 A1 | 12/2015 | Hindson et al. | |
| 2016/0024572 A1 | 1/2016 | Shishkin et al. | |
| 2016/0024761 A1 | 1/2016 | Korb | |
| 2016/0053253 A1 | 2/2016 | Salathia et al. | |
| 2016/0060621 A1 | 3/2016 | Agresti et al. | |
| 2016/0130649 A1 | 5/2016 | Xie et al. | |
| 2016/0199838 A1 | 7/2016 | Handique et al. | |
| 2016/0251714 A1 | 9/2016 | Conant et al. | |
| 2016/0289669 A1 | 10/2016 | Fan et al. | |
| 2016/0314242 A1 | 10/2016 | Schnall-Levin et al. | |
| 2017/0044525 A1 | 2/2017 | Kaper et al. | |
| 2017/0307502 A1 | 10/2017 | Mason et al. | |
| 2017/0320038 A1 | 11/2017 | Husain et al. | |

U.S. PATENT DOCUMENTS

| | | |
|---|---|---|
| 2017/0321252 A1 | 11/2017 | Hindson et al. |
| 2017/0335385 A1 | 11/2017 | Hindson et al. |
| 2017/0356027 A1 | 12/2017 | Hindson et al. |
| 2018/0030515 A1 | 2/2018 | Regev et al. |
| 2018/0037942 A1 | 2/2018 | Fu |
| 2018/0051321 A1 | 2/2018 | Hindson et al. |
| 2018/0080075 A1 | 3/2018 | Brenner et al. |
| 2018/0094298 A1 | 4/2018 | Hindson et al. |
| 2018/0094312 A1 | 4/2018 | Hindson et al. |
| 2018/0105808 A1 | 4/2018 | Mikkelsen et al. |
| 2018/0112266 A1 | 4/2018 | Hindson et al. |
| 2018/0127744 A1 | 5/2018 | Hu et al. |
| 2018/0127823 A1 | 5/2018 | Shekhar et al. |
| 2018/0274027 A1 | 9/2018 | Hindson et al. |
| 2018/0282804 A1 | 10/2018 | Hindson et al. |

FOREIGN PATENT DOCUMENTS

| | | |
|---|---|---|
| EP | 2414548 A2 | 2/2012 |
| WO | 2018013723 A1 | 1/2018 |
| WO | 2018058073 A2 | 3/2018 |

OTHER PUBLICATIONS

International Search Report for PCT Application No. PCT/US2018/048353 dated Nov. 5, 2018.

* cited by examiner

*Primary Examiner* — Narayan K Bhat
(74) *Attorney, Agent, or Firm* — Jeffrey Schox

(57) ABSTRACT

A system and method for target material capture, the method comprising: receiving a set of target cells into an array of wells defined at a surface plane of a substrate; receiving a set of particles into the array of wells, thereby co-capturing the set of target cells and the set of particles; achieving a desired state for the array of wells upon receiving a washing fluid into a cavity in communication with the array of wells; receiving a lysis buffer into the cavity; receiving a partitioning fluid into the cavity, thereby displacing the lysis buffer from the cavity and partitioning each of the array of wells from adjacent wells, at the surface plane; and retaining intercellular material of the set of target cells, individually with the set of particles within the array of wells.

20 Claims, 11 Drawing Sheets

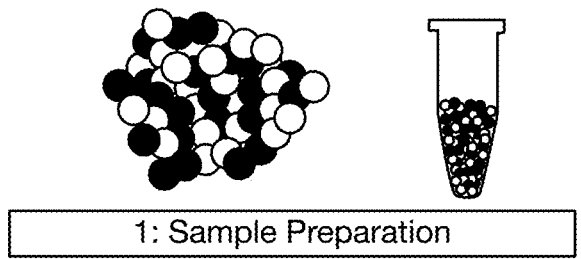

1: Sample Preparation

Dissociated Tissue
Single Cell Suspension
Optional antibody tagging of surface proteins

FIGURE 5A

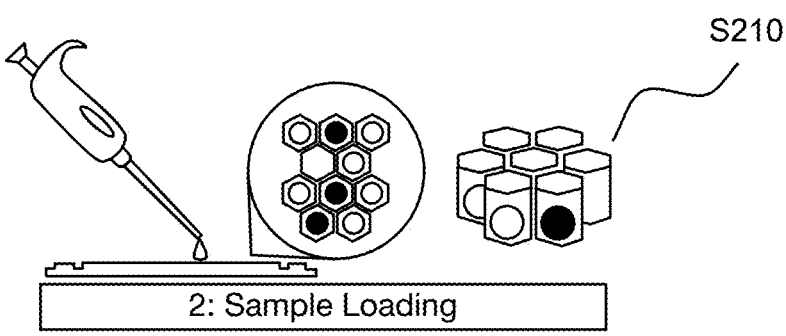

2: Sample Loading

Single cells are pipetted directly onto slide
Cells are isolated into wells via gravity
Optional sample loading QC by microscopy

FIGURE 5B

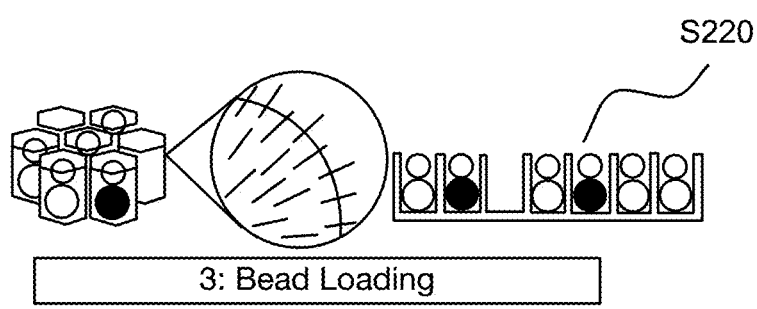

3: Bead Loading

Beads are pipetted directly onto slide containing single cells
Optional cell and bead loading QC by microscopy

FIGURE 5C

4: Slide Station Assembly

Slides are capped and inserted into slide station
Excess beads are washed away
Slide is ready for on-instrument lysis and RT

5: Cell Lysis

Cells are lysed and mRNA hybridizes to beads

6: RT Reaction

Each single cell is uniquely tagged with a cellular
Barcode and unique molecular indices Settle different cell types (e.g., mouse cells and human cells) into microwells through gravity settling.

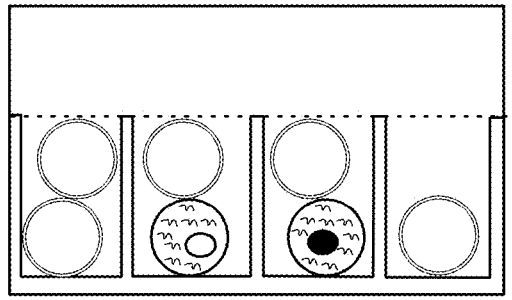

Settle barcoded beads into microcells by gravity

FIGURE 6C

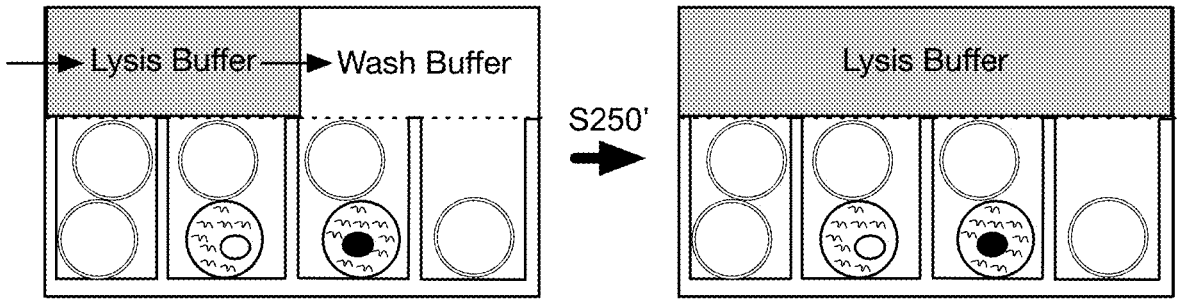

Pump cold (e.g., between 2C and 10C) lysis buffer (e.g., of a predetermined cocktail and concentration) over the microcells for a predetermined residence time (e.g., less than 30 seconds). The residence time and lysis concentration are important. The amount of lysis reagents delivered into the microcells is directly proportional to the concentration of lysis reagents and the residence time. The residence time is optimized such that enough lytic agents are delivered to microcells but not long enough for cells to lyse, release mRNA, and have it diffuse out of the microcells. The diffusion time of mRNA can optionally be slowed down by lowering the temperature and/or deepening the wells.

FIGURE 6D

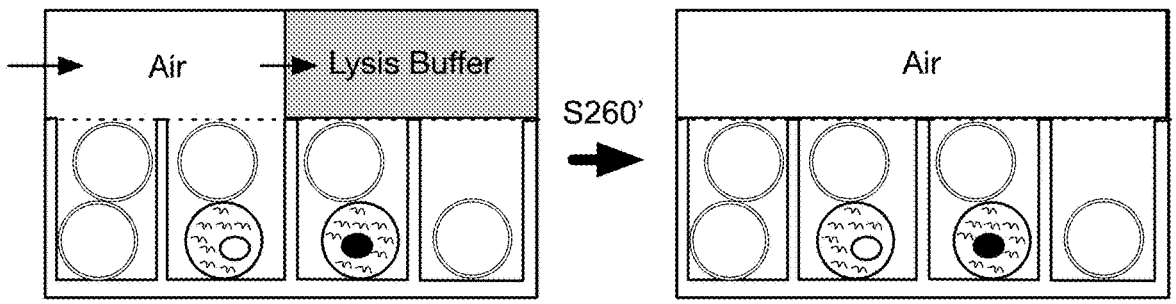

After lysis buffer resides over the microwells for a predetermined amount of time (e.g., between 5 and 60 seconds), air is pumped over the microwells to remove the lysis buffer and partition the microwells from each other.

FIGURE 6E

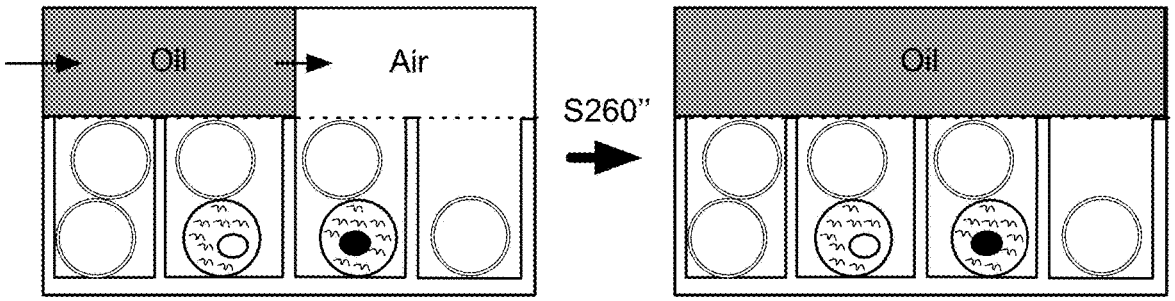

Oil is pumped over the microwells to partition the microwells from each other. Oil helps prevent evaporation of liquid from the microwells during an incubation time (e.g., long incubation time) described in FIGURE 3G.

FIGURE 6F

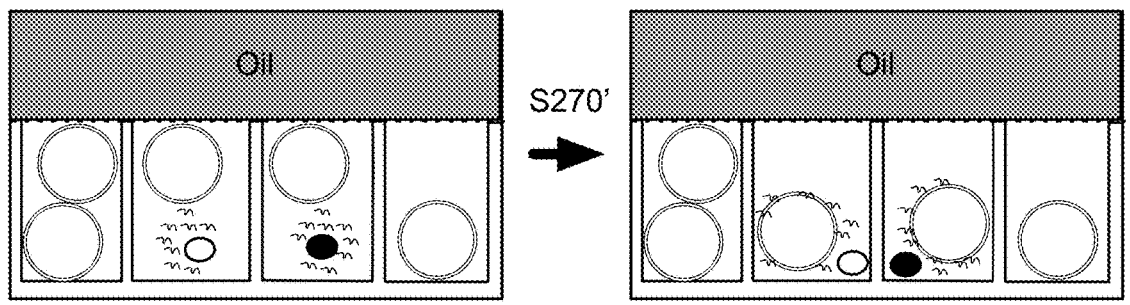

The temperature of the microwells is increased (e.g., to 26C) and held (e.g., for between 15 and 30 minutes). The cells lyse, thereby releasing mRNA. The mRNA starts to bind the oligonucleotide fragments of the bead through Poly A (present on mRNA) and Poly T (present on the bead) interactions. The oil partition prevents mRNA from one well escaping to neighboring wells.

FIGURE 6G

SYSTEM AND METHOD FOR LEAKAGE CONTROL IN A PARTICLE CAPTURE SYSTEM

CROSS-REFERENCE TO RELATED APPLICATIONS

This application claims the benefit of U.S. Provisional Application No. 62/834,824 filed on 16 Apr. 2019, which is incorporated in its entirety herein by this reference.

TECHNICAL FIELD

This invention relates generally to the cell capture and cell processing field, and more specifically to a new and useful method for leakage control within the cell capture and cell processing field.

BACKGROUND

With an increased interest in cell-specific drug testing, diagnosis, and other assays, systems and methods that allow for individual cell isolation, barcoding, identification, and retrieval are becoming highly desirable. Single cell capture systems and methods have been shown to be particularly advantageous for these applications. However, drifting of biological target material (e.g., material derived from cells post-cell lysis, cell-free nucleic acid material, etc.) can be particularly problematic in these systems and methods, resulting in non-specific capture of target material (e.g., messenger ribonucleic acid [mRNA], proteins, etc.), and/or leakage of target material between chambers or partitions of a capture device.

Thus, there is a need in the cell capture and cell processing field to create a new and useful system and method for leakage control while capturing and/or processing cells.

BRIEF DESCRIPTION OF THE FIGURES

FIGS. 5A-5H depict a variation of a method for single cell capture and processing, with leakage control;

FIGS. 6A-6G depict a variation of a system and method for single cell capture and processing, with leakage control.

DESCRIPTION OF THE PREFERRED EMBODIMENTS

The following description of the preferred embodiments of the invention is not intended to limit the invention to these preferred embodiments, but rather to enable any person skilled in the art to make and use this invention.

1. System

Figure 1A:
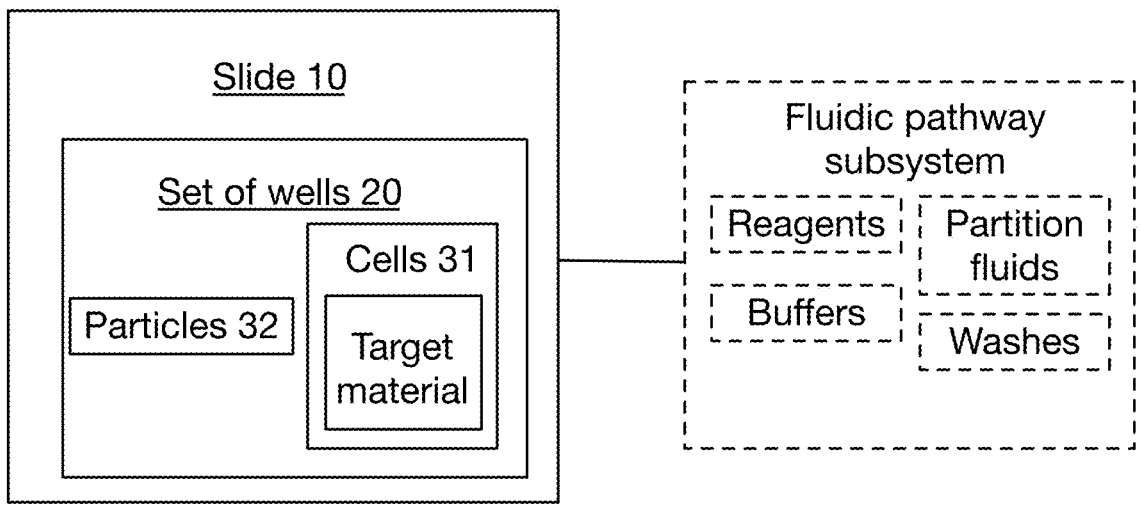
FIG. 1A is a schematic representation of an embodiment of a system for single cell capture and processing, with leakage control.

As shown in FIG. 1A, an embodiment of a system for single cell capture and processing includes a slide 10 defining a set of wells 20 configured to receive any or all of: a set of cells 31, a set of particles 32, and any other suitable materials (e.g., reagents). Additionally or alternatively, the system can include any or all of the system components described in U.S. application Ser. No. 16/048,104, filed 27 Jul. 2018; U.S. application Ser. No. 16/049,057, filed 30 Jul. 2018; U.S. application Ser. No. 15/821,329, filed 22 Nov. 2017; U.S. application Ser. No. 15/782,270, filed 12 Oct. 2017; U.S. application Ser. No. 16/049,240, filed 30 Jul. 2018; and U.S. application Ser. No. 16/115,370, filed 28 Aug. 2018, which are each incorporated in their entirety by this reference.

Figure 1B:
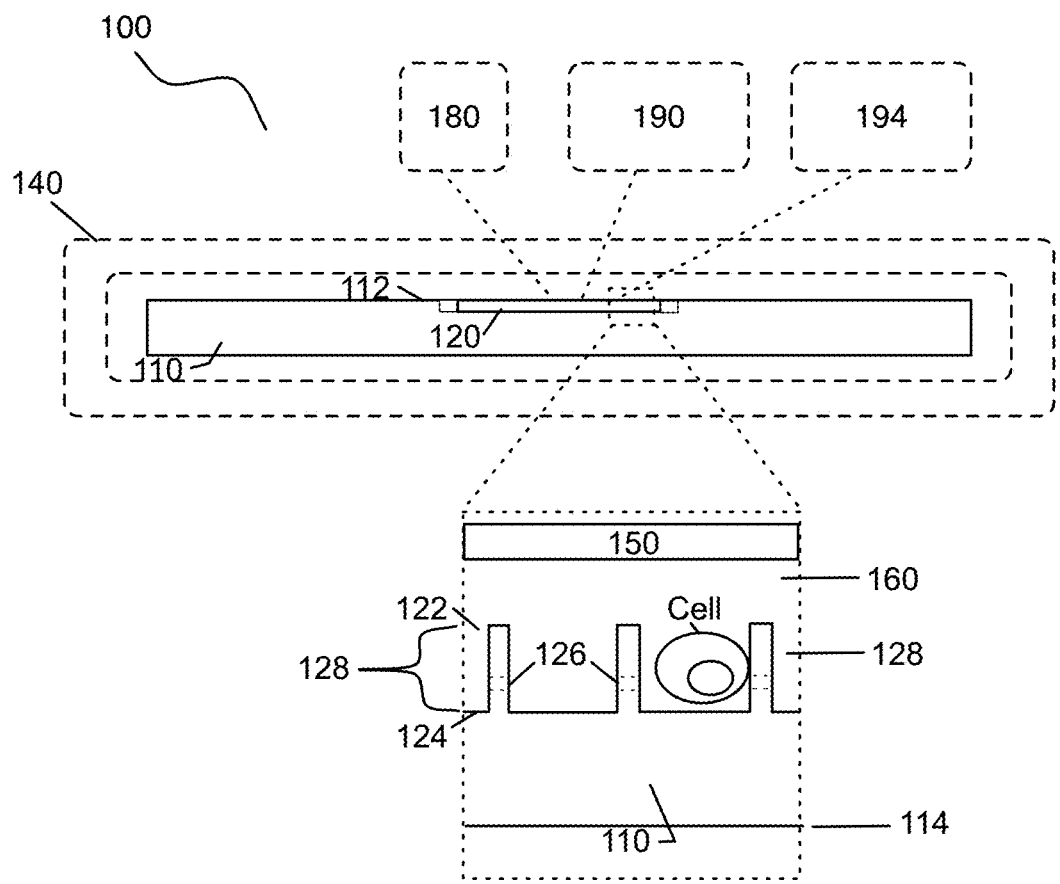
FIG. 1B is a schematic representation of an embodiment of a system for single cell capture and processing, with leakage control.

In more detail, with respect to an embodiment shown in FIG. 1B, a system 100 for isolating and analyzing a set of cells includes: a substrate 110 having a broad surface; an array of wells 120 defined at a first side 112 (e.g., upper broad surface) of the substrate, each well 128 in the array of wells 120 including an open surface 122 defined at the first side 112, a base surface 124 defined within the substrate proximal a second side 114 (e.g., lower broad surface) directly opposing the first side 112, and a set of walls 126 extending between the base surface 124 and the open surface 122 to form a well cavity of the well 128. The array of wells 120 can be arranged in an active region of the substrate, or in any other suitable arrangement. To facilitate sample or fluid delivery to the array of wells 120, the system 100 can further include a fluid delivery module 140 configured to couple to the substrate 110 and transfer a sample containing the set of cells and/or another fluid to the array of wells 120. Additionally or alternatively, the system 100 can include a flow control subsystem (e.g., pressure pump system) 180 configured to control fluid (e.g., biological sample, process reagent, solution containing non-cell particles) flow (e.g., direction, velocity, volume of the fluid) through the system 100, as well as any other suitable flow through the system requiring control and/or actuation. Additionally or alternatively, the system 100 can include a thermal control module 190 for controlling the temperature of portions of the system 100. Additionally or alternatively, the system 100 can include an imaging subsystem 194 configured to perform optical imaging, illumination, or irradiation of the contents of the array of wells 120, and to enable identification, localization, and quantification of cells retained by wells of the array of wells 120. Additionally or alternatively, the system 100 can include an extraction module that can extract one or more: target cells, particles, cell-particle pairs, genetic complexes, and/or genetic products from the array of wells. However, variations of the system 100 can include any other suitable component in any suitable configuration and/or combination, as described in U.S. application Ser. No. 15/333,420 entitled "Cell Capture System and Method of Use" and filed 25 Oct. 2016, U.S. application Ser. No. 14/208,298 entitled "System for capturing and analyzing cells" and filed 13 Mar. 2014, and U.S. application Ser. No. 14/289,155 entitled "System and Method for Isolating and Analyzing Cells" and filed 28 May 2014, which are each incorporated in their entirety by this reference.

The system embodiments described function to prevent non-specific capture of target material (e.g., messenger ribonucleic acid [mRNA], proteins, etc.), and/or leakage of target material between wells of the system, in order to facilitate performance of downstream sample processing steps. The system embodiments described are configured to perform the steps of the method embodiments described in Section 2 below, and/or any other suitable method.

The system embodiments described also function to isolate, capture, retain, and analyze cells of a cell population, in at least one of single-cell format and single-cluster format, at known, addressable locations, and further to facilitate performance of multiple single-cell assays that can be performed on individual target cells (e.g., rare cells in a biological sample) or clusters of cells (e.g., doublets, triplets). In preferred embodiments, the system 100 functions to facilitate the preparation of genetic libraries (e.g., cDNA generated from captured mRNA from lysed target cells, amplified cDNA, amplified DNA) of captured single cells for sequencing proximately following, and within the same device, as cell capture. Once cells are captured in defined locations determined by single cell capture wells, the fluid delivery module of the system 100 can be used to provide and deliver reagents simultaneously, sequentially, and/or in repetition to enable a variety of cellular, sub-cellular or molecular reactions to be performed in each of the single cells/cell clusters. Additionally or alternatively, the system 100 can function to capture and process non-cell particles (e.g., nucleic acid material, other biological material, other non-biological material, particles containing molecular probes or reagents, etc.), as well as combinations of single cells and single non-cell particles (e.g., in co-capturing cell-particle pairs within individual microwells). Furthermore, the system 100 can enable controlled and rapid thermal modulation of the array of wells and additionally or alternatively of the fluid delivered to the array of wells (e.g., heating and cooling cycles from 95° C. to 1° C.), to maintain cell or biological material viability, increase efficiency of biological assays, and perform a variety of biochemical processes within the set of wells. The system 100 can also allow optical interrogation and detection of events on each of the captured cells at a single cell/single cluster level. The system 100 can additionally or alternatively enable selective release and/or selective removal of one or more of the captured cells or non-cell particles for further processing and analysis. For instance, the system 100 can enable co-capture of single cell and particles within individual wells, release of intracellular content (e.g., mRNAs, etc.) from cells through lysis steps, binding of intracellular content to barcoded probes of the particles, performance of reverse transcription (RT) reactions within the wells, and selective retrieval of target amplified content associated with the intracellular content from the wells.

In some embodiments, the system 100 can confer the benefits of real-time cell tracking, viable cell and/or other biological material retrieval, biochemical processes (e.g., cell lysis, cell fixation, polymerase chain reaction, reverse transcription, etc.) and selective molecular analysis (e.g., electrophoresis, sequencing, fluorescence imaging), either in the same microfluidic chip or off-chip. In some embodiments, the system 100 can be used to capture circulating tumor cells (CTCs) and subpopulations of CTCs, such as circulating stem cells (CSCs), but can additionally or alternatively be used to capture any other suitable cell (e.g., erythrocytes, monocytes, macrophages, osteoclasts, dendritic cells, microglial cells, T-cells, B-cells, megakaryocytes, germ cells, nurse cells, neural cells, stem cells, etc.) or biological material of possible interest. The system 100 is preferably defined on a substrate 110, more preferably a microfluidic chip, but can alternatively be located on or defined by any suitable substrate.

In specific examples, the system 100 can be used with method(s) operable for single cell molecular reactions, wherein such systems can facilitate high efficiency capture of cells (e.g., 100s, of cells, 1000s of cells, 10,000s of cells, 100,000s of cells, 1,000,000 of cells, etc.) in single cell format (or single cluster format) within wells, as well as on-chip reagent delivery to the wells, incubation, and thermocycling in order to provide a cell capture-to-molecular reaction workflow. In more detail, microfluidic and other portions of the system can be operable to perform assays (e.g., assays associated with ARV7 mRNA) using polymerase chain reaction (PCR) with sample (e.g., prostate clinical samples) with single cell or single cell cluster resolution. In specific examples, the system 100 can accommodate sample volumes as low as 10 µl to as high as on the order of up to 1 mL within a fluid reservoir 160 associated with the array of wells 120, wherein the sample can contain a range of between 500 to 10,000 target cells, thereby providing the ability to process larger sample volumes containing a large number of cells of interest.

The system can include and/or be configured to interface with any number or types of cells. The cells can include any or all of mammalian cells (e.g., human cells, mouse cells, etc.), embryos, stem cells, plant cells, or any other suitable kind of cells. The cells preferably contain target material (e.g., target lysate) which originates within the cells and is eventually released and captured by the cell capture system, but can additionally or alternatively include any other material within or on one or more cells. In some variations, the target cell material includes mRNA. Additionally or alternatively, the target cell material can include any suitable RNA, DNA, protein, or other material.

The system can additionally include and/or be configured to interface with a set of particles, which are each preferably functionalized with a set of probes configured to bind with target material of the cells. The probes preferably include nucleotides (e.g., polynucleotides, oligonucleotides, etc.); additionally or alternatively, the particles can be otherwise functionalized, not functionalized, or present in any other suitable format. The diameter of the particles is preferably substantially similar to (e.g., equal to) the well diameter, as described below, and/or the cell diameter. This diameter can be between 10 and 30 microns (e.g., 20 microns), such that only a single particle can enter each well containing a cell. Alternatively, the particle diameter is sized such that only a single particle can enter any well, multiple particles can enter each well, and the particles can have any suitable diameter (e.g., less than 10 microns, greater than 30 microns, variable, etc.). In related embodiments, a well is configured to co-capture a single cell and a single particle along (or predominantly along) a longitudinal axis of the well; however, a well can be configured in any other suitable manner.

The particles are preferably in the form of beads, further preferably in the form of microspheres, but the particles can additionally or alternatively include any other material in any suitable form. The particles can have any suitable set of properties, such as any suitable physical properties (e.g., non-swelling behavior, dissolvability, etc.), magnetic properties, optical properties, surface properties (e.g., porous, non-porous, pores of certain size ranges, etc.), chemical properties (e.g., biocompatibility, surface functional groups, binding affinities, etc.), thermal properties, or other properties. In some variations, the particles are barcoded with a unique barcode (e.g., using biopolymer composites, functionalized or otherwise processed). The particles can include any or all of: polystyrene, glass, PMMA, polymer with a magnetic core, polymer with a hydrogel surface and/or a combination of one or more other suitable materials. In a specific example, the particles include monodisperse (+/− 10% Cv) 20-micron high-density BioBeads (HDBB)

The density of the particles is preferably greater than the majority or all of buffer solutions (e.g., initial buffer containing solution, solvent, etc.) and/or flow solutions used during the method 100, such that the particles are configured to enter and stay in individual microwells. Alternatively or alternatively, the particles can have a density less than one or more of the solutions, a variable density, or any other suitable density. In one variation, the particles include a set of HDBB particles with an optimal linker density configured to maximize binding between the HDBB and mRNA released from lysed cells. In another variation, the microspheres include glass beads with a polystyrene coating, and are approximately 20 microns (e.g., between 15 and 30 microns) in diameter. However, the system 100 can additionally or alternatively operate with any other suitable particle(s).

Individual cell and/or particle capture is preferably achieved by flowing or dispensing a sample containing a group of single cells within a fluid layer over the array of wells 120 in a direction parallel (e.g., substantially parallel, within 0.1 degrees of parallel, within 1 degree of parallel, within 45 degrees of parallel, completely parallel, etc.) to the broad surface of the substrate, and capturing the cells once they have descended through the fluid layer towards the array of wells 120 under the influence of gravity. Alternatively, individual cell capture can be achieved by delivering a sample containing a group of single cells into a fluid layer provided by a fluid reservoir 160, over the array of wells 120 in a direction perpendicular to the broad surface of the substrate, and capturing the cells once they have descended through the fluid layer towards the array of wells 120 under the influence of gravity. However, in some variations, individual cell capture can additionally or alternatively be achieved by any suitable mechanism for promoting single cell transfer into a well of the set of wells. Furthermore, the system 100 is preferably configured to prevent undesired fluid currents that can lift cells from the substrate or move cells/cell clusters from well cavities 128 at which the cells are captured and fully retained within. However, in some variations, the system 100 can be configured to facilitate moving of cells/cell clusters in any suitable manner. The flow path of a fluid (e.g., biological sample, process reagent) through the system 100 is preferably multi-directional and uniform, such that each cell/cell cluster in the system 100 experiences consistent conditions (e.g., gradient length scales along the flow path of flow properties such as pressure, density, temperature, solution composition, and other suitable properties are large relative to the length scales of the system); however, the flow path can alternatively be unidirectional, bi-directional, or have any other suitable characteristic(s).

Figure 2A:
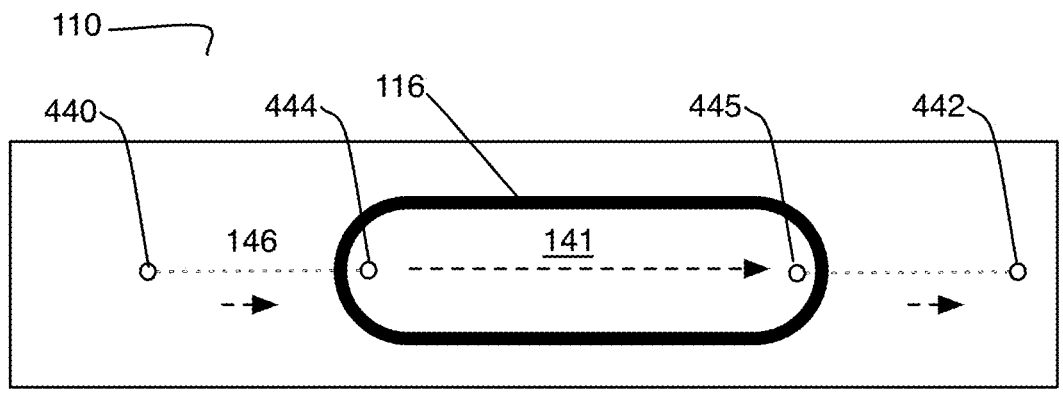
FIGS. 2A-2C depict variations of components of a system for single cell capture and processing, with leakage control.
Figure 2B:
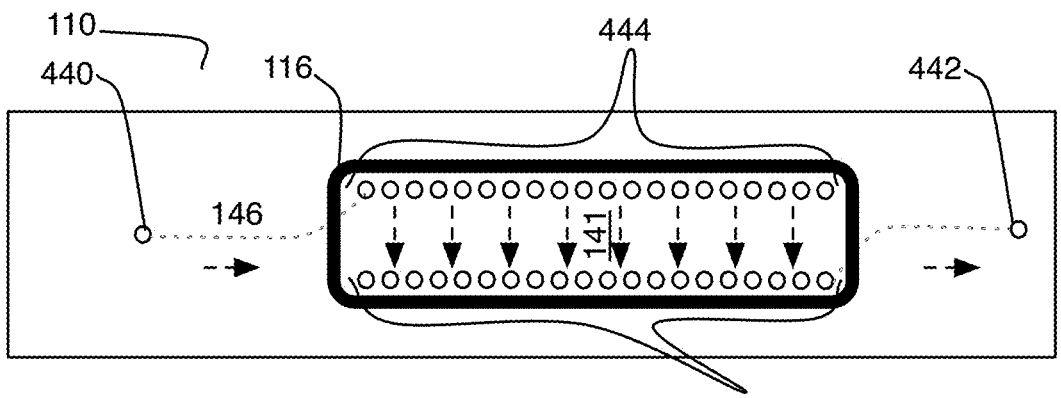
Figure 2C:
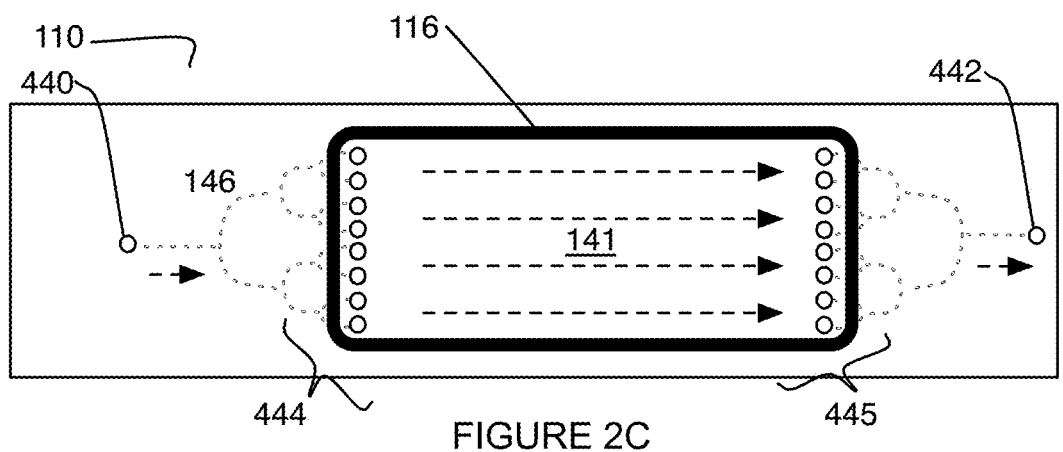

In variations of a specific example, as shown in FIG. 2A-2C, the flow path 141 of a fluid through the system includes a set of fluid pathways 146 (e.g., of a manifold coupled to the array of wells) of equal length (e.g., substantially equal length, equal length to within manufacturability tolerances, etc.) that are configured such that a reagent supplied at a manifold inlet 440 to the set of fluid pathways 146 arrives at each array of inlets 444 (e.g., a single well, along a region of a first edge of the reservoir, along region of a first edge of the active region of the substrate, etc.) at substantially the same time point (e.g., at the same time, within 1 second, within 1 minute, etc.), and passing across the active region 116 of the substrate (e.g., containing the array of wells 120) through an array of outlets 445 to a manifold outlet 442. Cell transport, isolation, sorting and viability maintenance can additionally be accomplished by controlling the sample flow rate through the system (e.g., by adjusting the flow rate so that a characteristic length scale of the flow is of a similar order as a characteristic length scale of a well, by dithering the flow rate between high and low flow conditions, etc.), or through any other suitable means. However, the flow characteristics of a fluid through system 100 may be otherwise configured.

In operation, the system 100 preferably receives a biological sample including a target cell population and facilitates distribution of the biological sample uniformly across the array of wells 120 (e.g., using uniform cross flow, smearing, a cytospin procedure, pipetting aliquots of the sample at different regions of the array etc.). However, the system 100 can additionally or alternatively facilitate distribution of the fluid (e.g., biological sample, process reagent, non-cell particles) across the set of wells using positive pressure (e.g., positive pressure at an inlet to the array) and/or negative pressure (e.g., negative pressure at an outlet of the array) applied by the flow control subsystem 180. Additionally or alternatively, actuation pressure that facilitates sample distribution can be cycled in a pulse-width modulation fashion or sinusoidal fashion to provide net actuation pressure, either net positive at the inlet or net negative at the outlet. As such, desired cells having a defining characteristic (e.g., size-based characteristic, density-based characteristic, adhesion-based characteristic, etc.) can be trapped within a well 128 as the biological sample flows across the array of wells 120. For example, in the variation of the system 100 configured to capture CTCs, the wells are preferably configured based upon defining morphological features of CTC cells, in order to facilitate capture and retention of CTCs in single cell or single cluster format. However, the system 100 can additionally or alternatively be configured to retain and facilitate processing or any other suitable particle of interest in any other suitable format. Actuation pressure is preferably provided by the flow control subsystem 180 (e.g., a manually-operated pipette, automated fluid-handling robot, vacuum pressure system, electromechanical micropump, etc.) in fluid communication with the system 100, but can alternatively or additionally be provided by any suitable mechanism.

In a variation, the system 100 receives a population of cells at a first density and/or overall number of cells that promotes capture of the population of cells at the array of wells 120 in single-cell format (e.g., with a density/overall number less than the number of wells in the array of wells 120). In this variation, the system 100 also receives a population of particles at a second density higher than the first density and/or overall number of particles that promotes co-capture of the population of cells with the population of particles. However, in other variations, the array of wells 120 can receive cells and/or particles in any other suitable manner. System components are described in more detail in the following sections.

1.1 System—Substrate

As shown in FIG. 1B, the substrate 110 functions to provide a medium at which the array of wells 120 (set of microwells, microwells, wells) can be defined. In variations, the substrate 110 can have a first side (e.g., upper broad surface) 112, and a second side (e.g., lower broad surface) directly opposing the first side. The upper broad surface 112 of the substrate 110 is preferably a planar surface, such that microfluidic elements (e.g., inlet, outlet, inlet manifold, outlet manifold, fluid channels, etc.) of the system 100 are defined at least partially at a planar surface. Alternatively, the upper broad surface 112 of the substrate 110 can be a non-planar surface, such that microfluidic elements of the system 100 are defined at least partially at a non-planar surface. In variations, the non-planar surface can be a concave surface, a convex surface, or a surface having concave, planar, and/or convex surfaces. Such variations can facilitate various methods of depositing and distributing a sample at the array of wells 120. In any variations of the substrate 110 including a non-planar upper broad surface 112, the non-planar portion(s) are preferably shallow (e.g., having a small depth relative to a width of the broad surface) or short (e.g., having a small height relative to a width of the broad surface); however, the non-planar portion(s) can additionally or alternatively include portions that are deep (e.g., having a large depth relative to a width of the broad surface) or tall (e.g., having a large height relative to a width of the broad surface). However, the surface can alternatively have any other suitable axis or type of symmetry, or can be asymmetrical.

The substrate 110 composition can provide desired characteristics relating to any one or more of: mechanical characteristics (e.g., substrate mechanical properties as a mechanical stimulus), optical properties (e.g., transparency), electrical properties (e.g., conductivity), thermal properties (e.g., conductivity, specific heat, etc.), physical characteristics (e.g., wettability, porosity, etc.), and any other suitable characteristic. The substrate 110 is preferably composed of a rigid material with high transparency (e.g., a transparent material, a translucent material), in order to facilitate imaging of the substrate 110 to analyze captured single cells/cell clusters. The high transparency material is preferably optically transparent, but can additionally or alternatively be transparent and/or translucent to other portions of the electromagnetic spectrum (e.g., microwaves, near infra-red, ultraviolet, etc.) In a few such variations, the substrate 110 can be composed of any one or more of: glass, fused silica, ceramic, a silicone-based material (e.g., polydimethylsiloxane (PDMS)), a polymer (e.g., agarose, polyacrylamide, polystyrene, polycarbonate, poly-methyl methacrylate (PMMA), polyethylene glycol, etc.), paper, a porous material, and any other suitable material, including composites thereof, with high transparency. Alternatively, the substrate 110 can be composed of any other suitable material having any other suitable optical properties. Additionally or alternatively, the substrate can be composed of any one or more of: a ceramic material, a semi-conducting material, a polymer, and any other suitable material.

The substrate 110 can be processed using any one or more of: etching methods, molding methods, printing methods (e.g., 3D printing processes), machining methods, and any other suitable manufacturing processes suited to a brittle, elastic, or ductile substrate material. Furthermore, features defined at the upper broad surface 112, including the array of wells, can be produced by any one or more of: molding, by polishing, by spinning a material in a flow phase followed by setting the material, by machining, by printing (e.g., 3D printing), by etching, and by any other suitable process. In a specific example, the array of wells 120 is defined within a silicon mold using a photolithographic process and deep reactive ion etching (DRIE) process to etch microfluidic elements into the silicon mold. In the specific example, the etched elements of the silicon mold are then transferred polymethylmethacrylate (PMMA) sheets as a substrate 110 using a hot embossing process. The substrate 110 in the specific example has dimensions of 3 inches by 1 inch, in order to substantially match dimensions of a glass microscope slide. In variations of the specific example, and/or for other variations of the array of wells 120, hot embossing of cyclic olefin polymer (COP) can be substituted for PMMA to form the microfluidic structures of the array of wells 120. However, the substrate 110 can alternatively be any other suitable substrate 120 processed in any other suitable manner.

Preferably, the substrate includes features that permit interaction (e.g., reversible or non-reversible attachment, coupling) to other subcomponents of system 100. In one variation, the substrate 110 can be coupled to components the fluid delivery module 140, wherein the substrate includes one or more inlets and outlets (examples of which are shown in FIGS. 2A-2C) to transmit fluid into and out of an active region of the substrate. In another example, the substrate 110 can be coupled to an adaptor 150 (shown in FIG. 1B) aligned above the array of wells to cooperatively define a fluid reservoir 160 to transfer fluid across the array of wells during operation of system 100, as described above.

The substrate 110 can additionally or alternatively be coupled to a substrate platform that functions to reversibly attach and align the substrate to a platform, heating element (e.g., thermal control module 190), and/or stage upon which assays are performed, wherein the stage can be used to physically adjust the position of the substrate within the system 100 to improve access of the array of wells to other elements of the system, such as the imaging subsystem 194, thermal control module 19o, and/or the extraction module. Preferably, the substrate platform can be configured to accommodate, secure, and manipulate substrates with various array configurations (e.g., arrays with 50,000 wells, arrays with 1M wells, etc.) with high precision, and can include an optional substrate attachment mechanism.

1.2 System—Array of Wells

The array of wells (set of microwells, microwells, wells) 120 functions to capture the set of cells in addressable, known locations such that the set of cells can be individually identified, processed, and analyzed. As such, the array of wells 120 is preferably configured to facilitate cell capture in at least one of a single-cell format and single-cluster (e.g., a cell-particle pair) format. However, the array of wells 120 can additionally or alternatively be configured to receive any other suitable type of particle, in any other suitable format. For instance, the array of wells 120 can be configured (e.g., sized, shaped) to receive mammalian cells, embyros, microspheres, particles, cell-particle pairs, and cells conjugated to microspheres.

As shown in FIG. 1B, the array of wells 120 is preferably defined at the upper broad surface 112 of the substrate 110, each well 128 in the array of wells 120 including a base surface 124 defined within the substrate and proximal a second side (e.g., lower broad surface 114), an open surface 122 directly opposing the base surface 124 and proximal the upper broad surface, and a set of walls 126 extending between the base surface and the open surface defining the well cavity 128 of the well.

The array of wells 120 is defined at an active region of the substrate 110, wherein the active region can be any suitable area (e.g., 1 square inch, 10 cm, 2 square inch, 3 square inch, 4 square inch, etc.) of the substrate (FIG. 2A-2C). Preferably, the active region (and the array of wells) of the substrate is accessible by other components of the system 100, including the imaging subsystem 194, fluid delivery module 140, thermal control module 190, and/or extraction module, in order to perform isolation, processing, and analysis of single captured cells. The array of wells 120 can include any suitable number of wells (e.g., on the scale of 100, 1,000, 100,000 wells, 50,000 wells, 100,000 wells, 1 million wells, 2 million wells, 3 million wells, 4 million wells, 5 million wells, 6 million wells, 7 million wells, 9 million wells, 10 million wells, etc.). In preferred variations, the array of wells includes at least 250,000 wells. In a specific example, the array of wells includes approximately 1 million wells. However, the array of wells can be configured in any other suitable manner.

In relation to the base surface 124 and the open surface 122, each well 128 preferably has at least one wall (e.g., a set of walls) 126 extending between the base surface 124 and the open surface 122. In a variation, as shown in at least FIG. 1B, the walls of each well 126 at least partially physically and fluidly separates an individual well 128 from at least one other adjacent well, defines a depth, width, and/or cross-sectional dimensions of the well, and are preferably perpendicular to a plane defined by the horizontal axis of the open surface 122. Preferably, the wall thickness of the walls 126 is between 4-5 micrometers, but can be any dimension less than 20 micrometers. The wall 126 can extend vertically from a plane defined by the open surface 122 to the base surface 124 to define the well cavity 128; as such, in some variations, a well cavity 128 of each well in the array of wells can be prismatic (e.g., cylindrical prismatic, hexagonal prismatic, polygonal prismatic, non-polygonal prismatic, etc.). In a specific example, the well cavity of each well defines a hexagonal prism with a depth greater than a sum of a particle diameter of the set of particles and a cell diameter of the set of target cells. However, the wall 126 can extend between the open surface 122 and the base surface 124 in any other suitable manner in other variations (e.g., curved walls, straight walls, bent walls, etc.). For instance, the a wall of the set of walls 126 can gradually reduce a characteristic dimension (e.g., diameter, horizontal cross section, vertical cross section) of the well from the open surface to the base surface (e.g., by forming discrete steps, by gradually adjusting the characteristic dimension in a linear or a non-linear manner with any suitable slope, etc.). However, in some variations, a well 128 may not have a well-defined wall 126 perpendicular to a plane defined by the open surface 122 (e.g., the base surface may extend in some manner directly to the open surface without forming a wall perpendicular to the open surface). In examples, the base surface 124 and the open surface 122 can be separated, with or without a wall, by a distance (e.g., height of a well cavity 128) of between 0.5 microns to 50 microns (e.g., approximately 25 microns for an application involving capture of single target cells, approximately 40 microns for an application involving capture of single cell-particle pairs). However, the wells of the array of wells can be configured with any other physical characteristic and/or dimension, in order to perform the isolation, processing, and analysis steps described in method 200. Additionally or alternatively, the set of walls can include a set of channels that fluidly couple each well to at least one adjacent well in the array of wells 120. In such variations, the channel(s) of a set of channels can be defined within a region of the substrate 110 between adjacent wells, or can be defined by overlapping portions of adjacent wells. In a specific example, a channel can have a characteristic dimension of 5 microns, and in variations of the specific example, a channel can have a characteristic dimension ranging from 0.5 microns to 75 microns.

Furthermore, the array of wells 120 is preferably arranged in a packed array, but can alternatively be arranged in any other suitable manner. In one example, the array of wells 120 can be arranged in a hexagonal close-packed array. In another example, the array of wells can be arranged in a rectangular array. In another example, the array of wells 120 can be arranged in any suitable irregular or non-uniform manner, for instance, to facilitate fluid flow from one portion of the array of wells 120 to another portion of the array of wells 120. In a specific example, the shortest distance of the center of each well to the center of an adjacent well of the array of wells is approximately 30 micron. However, the array of wells 120 can alternatively be arranged with any suitable spacing between wells (e.g., in a packed or a non-packed configuration), and in any other suitable manner.

Figure 3:
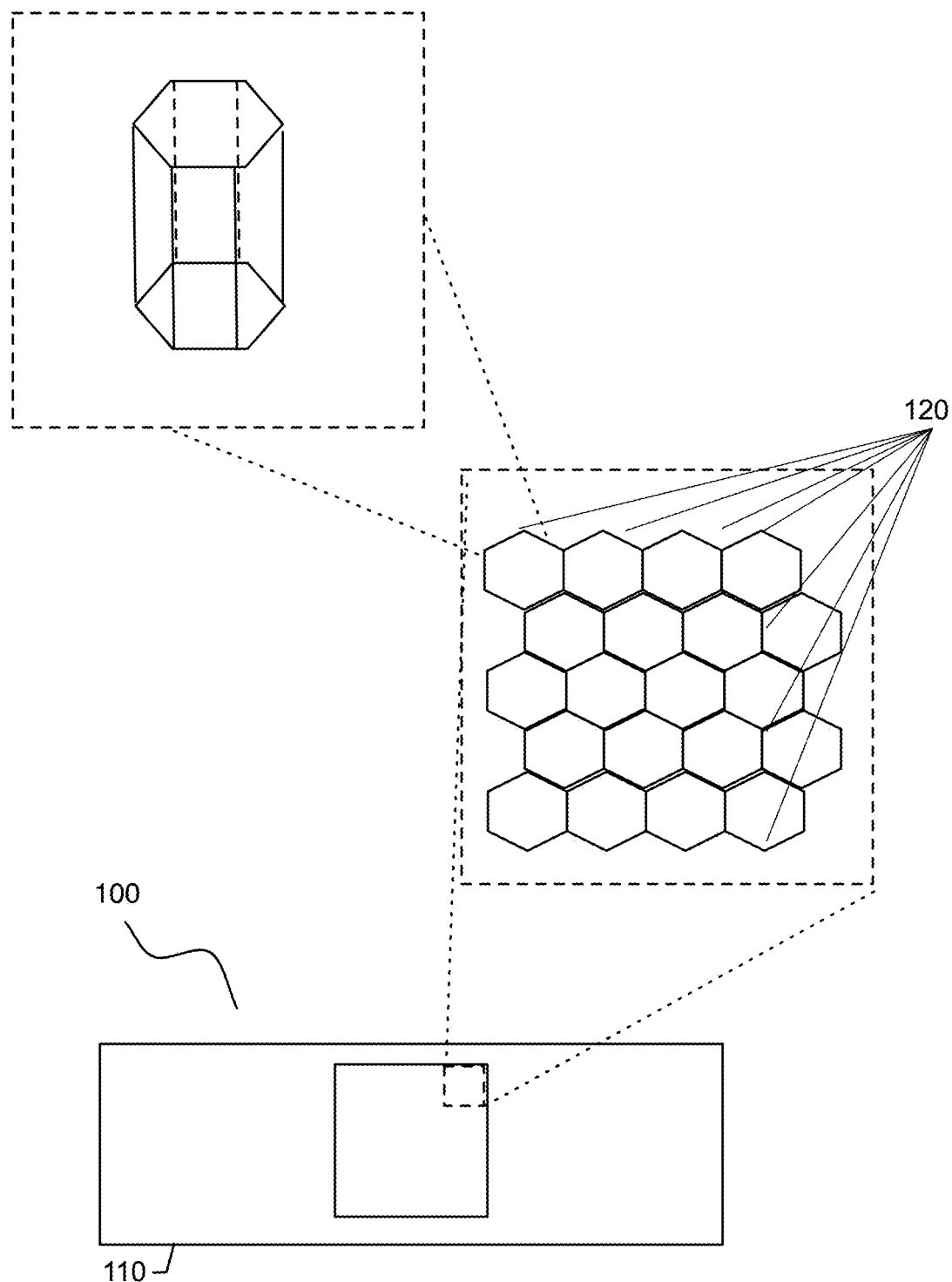
FIG. 3 depicts a specific example of components of a system for single cell capture and processing, with leakage control.

In a specific example configuration of the set of wells as shown in FIG. 3, the array of wells is arranged in a hexagonal close-packed configuration, wherein each well of the array of wells includes a hexagonal open surface aligned with the broad surface (e.g., surface plane 118) of the substrate. Furthermore, each well includes a hexagonal footprint at the base surface opposing the hexagonal open surface. Each well of the array of wells has a well cavity 128 that forming a hexagonal prism, including a set of walls approximately 5 micron in thickness, a height of approximately 40 micrometers, and a characteristic width of approximately 25 micrometers. The substrate defines 267,000 such hexagonal wells within an active region of the substrate that is approximately 150 square millimeters. However, the array of wells can be configured in any other suitable manner.

1.3 System—Fluid Delivery Module, Thermal Control Module, and Imaging Subsystem

The system 100 can include a fluid delivery module 140 that functions to transfer a sample containing the population of cells, population of particles, and/or another fluid, such as a process reagent and/or distribution fluid, to the array of wells 120, and can be coupled to the substrate 110. As such, the fluid delivery module can include one or more inlets, outlets, fluidic guides and/or structures that enable fluid transfer into, out of, and throughout various portions of the system.

The system 100 can additionally include thermal control module 190 that functions to heat and/or cool the substrate and its contents, in order to control the temperature of contents of the set of wells and/or fluid delivery module during operation of the system 100. In variations, the thermal control module can heat and/or cool a biological sample containing cells of interest and/or a fluid to facilitate cell capture and analysis, and can further function to facilitate reactions requiring cycling from low to high temperatures, such as for cell lysis, enzyme activations for probe hybridizations and thermocycling of biological sample mixtures for molecular diagnostic protocols, such as polymerase chain reaction (PCR). The thermal control module 190 can comprise a heater, a heat sink, a sensor, a fan, and one or more processors, however; the thermal control module can include any suitable component to sense and modulate the temperature of the array of wells, and according to any instruction (e.g., user-input, automatically, pre-set temperature schedule, according to a particular assay, etc.). In variations, the heater 192 of the thermal control module is preferably a thin heater (e.g., Peltier device) configured to controllably heat and cool the biological sample and/or fluid. The thermal control module 190 can additionally and or alternatively comprise a temperature sensor, or any other suitable element configured to facilitate temperature control. For example, the temperature sensor can couple to a heat-conductive substrate, to a heating element, or to a plate-shaped heater. Temperature control can be enabled using pulse-width modulation through fuzzy logic control, a proportional-integral-differentiation algorithm, or any other suitable means. Temperature control can be provided to a resolution of 1° C., or any other suitable resolution given the application.

The system 100 can additionally include an imaging subsystem 194 that functions to image the contents of the set of wells, and can further function to distinguish target objects (e.g., CTCs, labeled cells, microspheres) captured in the set of wells from other cells or objects in the sample introduced into the system 100. The imaging subsystem 194 preferably includes a fluorescence microscope, but can additionally or alternatively include any suitable imaging mechanism (e.g., an optical microscope, a CCD camera, a photodiode array, a light emitting diode, reflectors, one or more processors etc.). The fluorescence microscope is preferably operable (e.g., in an identification mode, a detection mode, etc.) to detect a fluorescence signal emitted from a target object one or more of the set of wells, and thereby identify that the well(s) contain(s) a target object. In a specific example, the imaging system (e.g., fluorescence imaging system) can be operable in a mode for providing real-time or near real-time fluorescence imaging of samples processed according to an assay. The imaging subsystem 194 is preferably positioned beneath the substrate and oriented to image the contents of the set of wells through the transparent (or translucent) material of the substrate; alternatively, the imaging subsystem 194 can be positioned above the substrate and oriented to image the contents of the set of wells unobstructed by the material of the substrate itself. However, the imaging subsystem 194 can be otherwise positioned in any suitable manner.

Other aspects of embodiments of components of the system 100 are described in further detail in U.S. application Ser. No. 16/115,059, filed 28 Aug. 2018, which are each incorporated in their entirety by this reference.

2. Method

Figure 4:
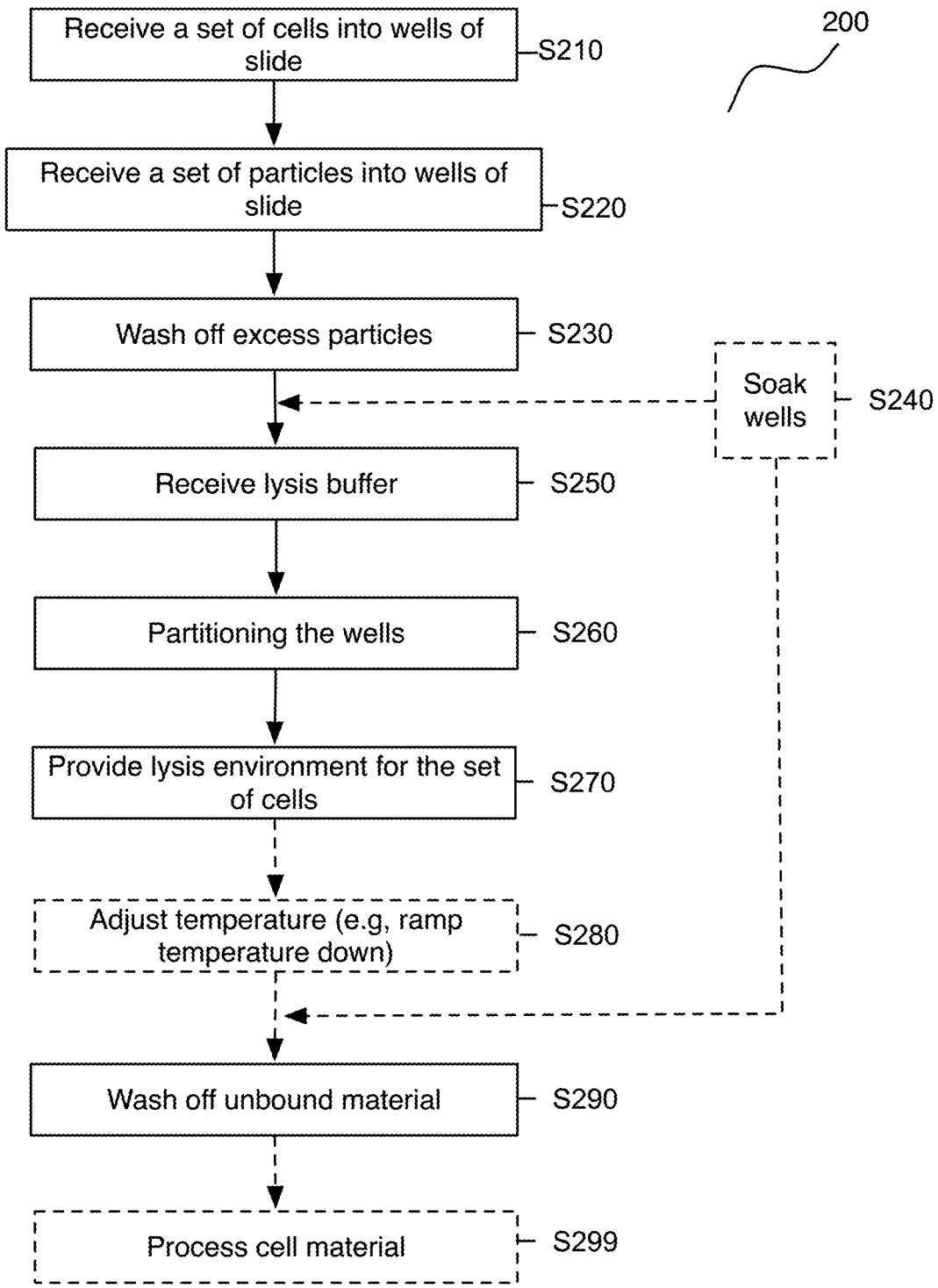
FIG. 4 is a schematic representation of an embodiment of a method for single cell capture and processing, with leakage control.

As shown in FIG. 4, a method 200 for single cell capture and processing includes receiving a set of cells into a set of wells S210; receiving a set of particles into the set of wells S220; receiving a washing fluid into a cavity in communication with the set of wells, thereby washing off excess particles S230 and any floating biomarkers (mRNA, proteins, etc); applying cold lysis buffer (temperature <15 C) to the set of cells S250; partitioning each of the array of wells S260; providing a lysis environment for the set of cells S270; and washing off unbound material S290. Additionally, the method 100 can include any or all of: soaking the contents of the wells S240; adjusting a temperature (e.g., ramping the temperature down) S280; processing the cell material (e.g., target cell material) S299; any of the processes described above in relation to the description of the system embodiments; and any other suitable process(es).

Figure 6A:
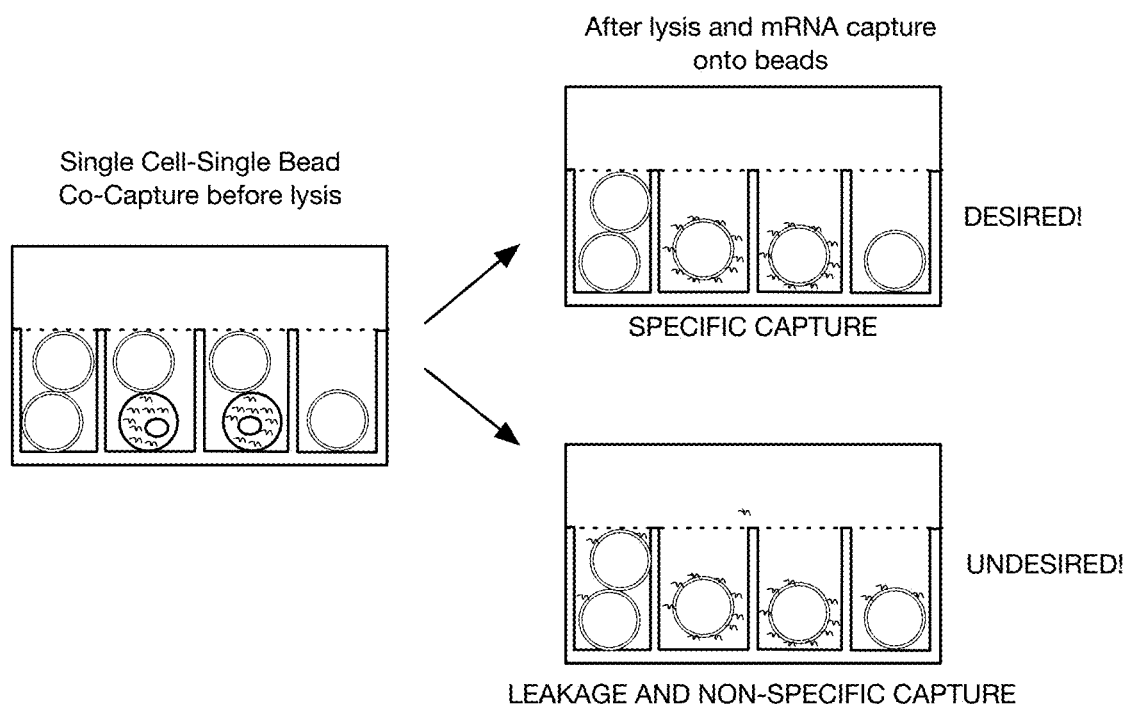

The method 200 functions to prevent non-specific capture of target material (e.g., messenger ribonucleic acid [mRNA], proteins, etc.), and/or leakage of target material between wells of the system, in order to facilitate performance of downstream sample processing steps. An example of a desired state of specific capture is shown in FIG. 6A (right, top), and an example of an undesired state of non-specific capture and leakage is shown in FIG. 6A (right, bottom). The method embodiments described are preferably implemented by one or more system embodiments described in Section 1 above, and/or any other suitable system components.

2.1 Method—Cell and Particle Loading

As shown in FIG. 4, the method 200 includes receiving a set of cells (including a subpopulation of target cells) into an array of wells of a slide S210, wherein, in an embodiment, Block S210 can include receiving, in single-cell format, target cells into an array of wells defined at a surface plane of a substrate, wherein each well in the array of wells extends perpendicular to and into the surface plane into the substrate. Block S210 can be implemented using embodiments of the substrate, array of wells, and/or fluid delivery module described above. Block S210 can additionally or alternatively be implemented by other system components.

The set of cells can include target cells of interest described above, and/or any other suitable cells, tissues, or other biological material (e.g., non-cellular biological material). As shown in FIG. 5A, in one variation, the set of cells can be derived from dissociated tissue, processed into a single-cell suspension, with optional antibody tagging of surface proteins; however, the set of cells can additionally or alternatively be derived from any other suitable source and/or processed in any other suitable manner. The set of cells can also include cells from the same species or different species (as shown in FIG. 6B).

Receiving the set of cells preferably includes underloading the set of cells relative to the number of wells of the slide (e.g., target less than 10% occupancy of wells, target less than 20% occupancy of wells, target less than 30% occupancy of wells, etc.), in order to promote capture of cells in single cell format across the array of wells. The process for cell loading is configured to maintain the viability of the cells by using gentle loading processes (e.g., gravity loading, low centrifugation, etc.), and to maintain the viability of cells after loading. Cell loading can include any or all of: gravity-induced entry (e.g., pipetting), low centrifugation, magnetic attraction, a force application (e.g., along an axis parallel to a broad surface of the slide, along an axis perpendicular to a broad surface of the slide, etc.), changing an orientation of the slide (e.g., cytospinning, tilting, rocking, etc.), or any other suitable process. In a first example, loading the set of cells includes pipetting aliquots between 50 and 500 microliters each into the wells. Loading the set of cells can also include loading any suitable buffer or other fluid.

As shown in FIG. 5B, receiving the set of cells can include performing a quality control operation, using the imaging subsystem described above, in order to observe proper loading of the set of cells across the array of wells. However, Block S210 can additionally or alternatively include any other suitable quality control operation (e.g., with a sensor-based approach) to determine proper loading of the set of cells across the array of wells.

As shown in FIGS. 4, 5C, and 6C, the method 200 further includes receiving a set of particles into the wells of the slide S220, thereby co-capturing the set of target cells and the set of particles across the array of wells. As shown in the FIGURES, the wells of the array of wells are high aspect ratio, such that the set of cells are configured to sit within wells at an inferior region, and the set of particles are configured to sit above the set of cells at a superior region of a well (for a well containing a single cell and a single particle in a desired state), thereby preventing lateral positioning of a cell and particle within the same plane within a well; however, the wells can be configured in another manner, with respect to co-capture of the set of cells and the set of particles across the array of wells.

The set of particles are preferably overloaded with respect to the cells (e.g., bead concentration is particle suspension is higher than cell concentration in cell suspension), but can additionally or alternatively be underloaded with respect to the cells, overloaded with respect to the number of wells, underloaded with respect to the number of wells, or otherwise loaded (e.g., in batches). The bead concentration to cell concentration ratio can be between 10:1 and 20:1. Alternatively, the bead concentration to cell concentration can be less than or equal to 10:1, greater than or equal to 20:1, or of any other suitable ratio.

Receiving the set of particles is preferably performed contemporaneously with (e.g., at the same time, at least partially overlapping in time, etc.) receiving the set of cells in Block S210, as reducing time between cell loading and particle loading can function to prevent unwanted lysis of cells. Alternatively, receiving the set of particles can be performed after Block S210, before S100, with a time delay (e.g., of less than five minutes, between 0 and 60 minutes, greater than 60 minutes, etc.) with respect to Block S210, or at any other suitable time(s). Receiving the set of particles can include any or all of the loading processes described above for cell loading (e.g., gravity loading) or any other suitable loading process.

In one variation, a set of particles are loaded into wells of the slide through a gentle loading process (e.g., gravity loading) after a set of cells were loaded into the wells through the same gentle loading process. In a specific example, the set of cells were underloaded with respect to the set of wells and the set of particles were overloaded with respect to the set of cells.

In an alternative variation, the set of cells and set of particles are loaded together (e.g., from the same suspension). However, Blocks S210 and S220 can additionally or alternatively be performed in any other suitable order or manner.

As shown in FIG. 5C, receiving the set of particles can include performing a quality control operation, using the imaging subsystem described above, in order to observe proper loading of the set of particles (e.g., with respect to the set of cells) across the array of wells. However, Block S220 can additionally or alternatively include any other suitable quality control operation (e.g., with a sensor-based approach) to determine proper loading of the set of cells across the array of wells.

2.2 Method—Excess Particle Removal and Well Soaking

Figure 5D:
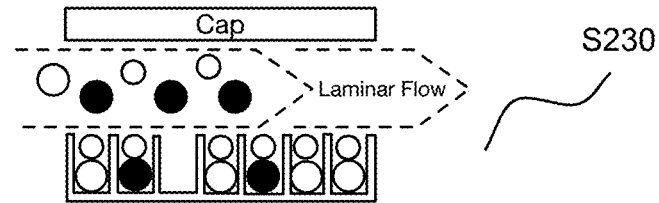
Figure 6B:
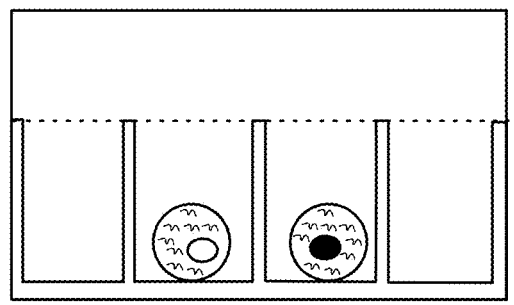

As shown in FIGS. 4 and 5D, the method 200 can optionally include washing off excess particles S230, which functions to remove any floating excess particles above the wells (e.g., fully above wells, partially exposed from the wells, etc.). As such, Block S230 includes achieving a desired state for the array of wells upon receiving a washing fluid into a cavity in communication with the array of wells and transmitting excess particles of the set of particles away from the array of wells. Block S230 can additionally or alternatively function to remove any other excess matter (e.g., floating cell material from prematurely lysed cells, debris, etc.). The wash or washes used in Block S230 can include any suitable buffer, liquid (e.g., water, oil, etc.), air, or any other suitable substance. The wash flow rate is preferably configured to remove material above walls of the wells without removing materials (e.g., cells, particles, buffers, liquids, etc.) from within the wells; additionally or alternatively, the wash flow rate can be configured to prevent entry of one or more wash buffers into the set of wells. As such, the wash is preferably applied in a laminar flow process (as shown in FIG. 5D), but can additionally or alternatively include or induce turbulent flow. The flow rate is preferably less than 100 microliters per second, but can alternatively be equal to 100 microliters per second, greater than 100 microliters per second, or have any other suitable flow rate. Additionally or alternatively, any other suitable parameters such as other flow parameters (e.g., flow duration), structural parameters (e.g., diameter of one or more fluidic pathways, arrangement of fluidic pathways, location of fluidic pathways over the set of wells, well height, well width, etc.) can be configured to prevent egression of one or more materials from the wells.

In a first variation, the characteristic length scale of the flow is of a similar order as a characteristic length scale (e.g., height, width, etc.) of a well.

The method 200 can optionally include soaking the contents of the wells S240, which can function to prevent cells from lysing prior to a desired time point (e.g., before lysis buffer delivery, during lysis buffer delivery, etc.), allow time for cells and/or particles to settle within the set of wells, or perform any other suitable function. The wells can be soaked with a wash buffer (e.g., as used above for washing off excess particles), a different buffer (e.g., initial buffer used with loading cells and/or particles, cell suspension buffer, particle suspension buffer, etc.), water, or any other suitable fluid. Block S240 can be performed after Block S230, before Block S230, during Block S230, multiple times during the method, or at any suitable point during the method. Alternatively, the method can be performed in absence of Block S240. In a first variation, the wells are soaked at 4 degrees Celsius for 11 minutes after Block S230; however, the soaking process can be performed using another suitable temperature, duration, or other soaking parameter.

2.3 Method—Cell Lysis with Well Partitioning for Leakage Prevention

Figure 5E:
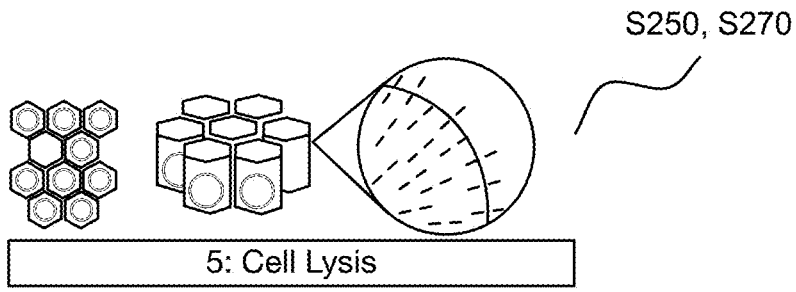

As shown in FIGS. 4, 5E, and 6D, the method 200 includes receiving a lysis buffer at the array of wells, thereby delivering the lysis buffer to the cells S250, which functions to initiate lysis of the cells (e.g., immediately, after a time delay, etc.), thereby enabling release of target cell material to be captured by the set of particles. As such, Block S250 can contribute to providing a lysis environment for the set of cells upon receiving a lysis buffer into the cavity (e.g., reservoir described above) in fluid communication with the array of wells. The lysis buffer is preferably received with flow parameters (e.g., flow rate, flow volume, duration of flow, etc.) configured to permit lysis buffer to enter the wells without removing contents from the wells. Block S250 preferably includes flowing a lysis buffer over the set of wells (e.g., within a cavity or reservoir situated above the array of wells in the orientation shown in FIG. 1B), but can additionally or alternatively include flowing lysis buffer through a set of wells, directly into a set of wells (e.g., from above, from below, etc.), or otherwise applying lysis buffer to the cells, using other fluid channels or flow pathways. In preferred variations, the lysis buffer is preferably applied through laminar flow, but can additionally or alternatively include or induce turbulent flow. The lysis buffer is preferably applied through the same fluid manifold (e.g., fluidic reservoir, fluidic pathways, fluidic reservoir fluidly connected to a set of fluidic pathways, etc.) that is used in Block S230, but alternatively another fluid manifold fluidly connected to the wells can be used. Additionally or alternatively, any or all of the fluid delivery subsystems (e.g., reservoir, fluidic pathways, etc.) described in the following can be used: U.S. application Ser. No. 16/048,104, filed 27 Jul. 2018; U.S. application Ser. No. 16/049,057, filed 30 Jul. 2018; U.S. application Ser. No. 15/821,329, filed 22 Nov. 2017; U.S. application Ser. No. 15/782,270, filed 12 Oct. 2017; U.S. application Ser. No. 16/049,240, filed 30 Jul. 2018; and U.S. application Ser. No. 16/115,059, filed 28 Aug. 2018, which are each incorporated in their entirety by this reference.

As shown in FIG. 6D with respect to Block S250', the lysis buffer is preferably chilled (e.g., to 4 degrees Celsius, to less than 10 degrees Celsius, between 0 and 20 degrees Celsius, greater than 20 degrees Celsius, etc.), which functions to slow down the diffusion time of target cell material (e.g., mRNA) from the cells and/or the set of wells. The structure (e.g., depth, width, shape, shape, etc.) of the wells can additionally or alternatively be configured to slow down the diffusion time of mRNA. The concentration of the lysis buffer is preferably configured to prevent cell lysis during the lysis buffer delivery time. The lysis buffer preferably includes one or more lytic agents, such as any or all of: Triton X-100 (e.g., 1%, less than 1%, greater than 1%, etc.), sodium deoxycholate [DOC] (e.g., 0.1%, less than 0.1%, greater than 0.1%, etc.), sodium dodecyl sulfate [SDS] (e.g., 0.2%, less than 0.2%, greater than 0.2%, etc.), or any other suitable lytic agent. Additionally or alternatively, the lysis buffer can include any or all of: Tris (e.g., 100 mM, less than 100 mM, greater than 100 mM, pH 7.5, pH less than 7.5, pH greater than 7.5, etc.), lithium chloride [LiCl] (e.g., 500 mM, less than 500 mM, greater than 500 mM, etc.), ethylenediamine tetraacetic acid [EDTA] (e.g., 2 mM, less than 2 mM, greater than 2 mM, etc.), dithiothreitol [DTT] (e.g., 5 mM, less than 5 mM, greater than 5 mM, etc.), and/or any other suitable reagent or component.

In one variation, the lysis buffer includes 100 mM Tris of pH 7.5, 500 mM LiCl, 1% Triton X-100, 2 mM EDTA, 0.1% DOC, 0.2% SDS, and 5 mM DTT. However, variations of the lysis buffer can include modified components and/or concentrations of components.

As shown in FIG. 6D, the residence time of the lysis buffer (e.g., time before S280, time before S290, etc.) is preferably less than or equal to 60 seconds (e.g., between 5 and 60 seconds), further preferably less than or equal to 30 seconds (e.g., between 5 and 30 seconds, 20 seconds, 15 seconds, 10 seconds, 5 seconds, etc.). Alternatively the residence time can be greater than 30 seconds, greater than 60 seconds, or have any other suitable value.

In one variation, described in relation to FIG. 6D, the lysis buffer is optimized such that enough lytic agents are delivered to the set of wells during the lysis buffer delivery time, but not long enough to initiate lysing the cells. Additionally or alternatively, the lysis buffer can include enough lytic agents to deliver to the wells, but not long enough to release target cell material (e.g., mRNA), have target cell material diffuse out of the wells, or have any other suitable outcome. The amount (e.g., volume, duration of delivery, etc.) of lysis buffer applied is preferably determined based on the concentration of the lysis buffer, Diffusivity of the critical lytic agent and the residence time of the lysis buffer over the microwells, but can alternatively be variable or otherwise determined. In another embodiment, the lysis buffer is configured to be in inactive state during its delivery and made active afterwards by any or all of: heat, light, the addition of a lysis reaction initiator, or any other suitable process or agent. Furthermore, in some embodiments, the lysis buffer is pre-cooled below 15° C. prior to entering the cavity over the microwells.

As shown in FIG. 4, the method 200 further includes partitioning the wells S260, which functions to isolate adjacent wells and their contents from each other and prevent the drifting of material (e.g., target cell material, cellular debris, particles, etc.) out of the wells (e.g., upward drifting out of wells) and into another well. As such, Block S260 can include partitioning each of the array of wells from adjacent wells of the array of wells, upon displacing the lysis buffer from the cavity or reservoir in fluid communication with the array of wells, with a partitioning fluid (e.g., gas, immiscible liquid). Block S260 can additionally or alternatively function to remove excess lysis buffer (e.g., lysis buffer outside out wells), maintain adjacent well separation during a lysis buffer incubation period, or perform any other suitable function. Block S260 is preferably performed during performance of Block S250 or a predetermined time period after performance of Block S250 (e.g., 5-60 seconds after), but can additionally or alternatively be performed at any other suitable time(s) during performance of the method 200.

Block S260 can include introducing one or more barriers over the wells, for instance, with the cavity or reservoir in fluid communication with the array of wells. The barrier can include a physical barrier, secondary fluids (e.g., partitioning fluid), or any suitable barrier. The barrier can be introduced into the same manifold associated with one or more of Blocks S210, S220, and/or S230, or be otherwise introduced. Secondary fluids can include any or all of gases, liquids (e.g., nonpolar, polar, viscous, non-viscous, etc.), colloids, or any other suitable fluid. Secondary fluids may include non-settling particles containing target biomarker scavenger that can bind any target biomarker egressing from any of the microwells.

Block S260 preferably includes dispensing (e.g., through a fluidic pathway subsystem) a partitioning fluid (e.g., air, oil, buffer, water, etc.), proximal to (e.g., above) each of the set of wells, (in the orientation shown in FIG. 6E with respect to S260' and FIG. 6F with respect to S260"), which functions to form a barrier (e.g., semi-permeable, non-permeable, selectively permeable, etc.) to prevent one or more contents of the wells from drifting out of the wells. In one variation, a partitioning fluid (e.g., air) achieves this barrier based on a flow rate of the partitioning fluid (e.g., as shown in FIG. 6E with respect to S260'). In a specific example, pumping a partition fluid over the set of wells with a flow rate above a predetermined threshold functions to prevent materials within a well from drifting up and exiting the well. Additionally or alternatively, the flow rate can function to remove materials (e.g., in a horizontal direction) that may drift above the walls before the materials could drift into another well. In a second variation, a partition fluid achieves a barrier by preventing evaporation of liquid from the wells (e.g., during a long incubation step). This can be achieved by any or all of: a density of the partition fluid (e.g., wherein the partition fluid is less dense than the lysis buffer), a weight of the partition fluid, a pressure achieved by the partition fluid, a temperature of the partition fluid and/or the slide (e.g., chilled slide), or any other suitable feature.

Block S260 preferably partitions material along a vertical axis (e.g., is a horizontal partition), wherein the partition is located at the height of one or more walls defining the set of wells. Additionally or alternatively, a partition can be established below a height of one or more walls (e.g., within a well), above a height of one or more walls, at a variable height, or at any other suitable location. Further additionally or alternatively, Block S260 can include partitioning material along a horizontal axis, along another axis, or in any other suitable way. In a first variation (e.g., as shown in FIGS. 6E-6F), materials (e.g., air as in FIG. 6E and oil as in FIG. 6F) provide well partitioning along a vertical axis, wherein the partition is established at a height corresponding the terminating portions of walls of the wells.

Block S260 can be enabled, at least in part, by a fluidic pathway subsystem interfacing with the slide (e.g., location and arrangement of fluidic pathways, number of fluidic pathways, length of fluidic pathways, diameter of fluidic pathways, fluidic pathway subsystem within the slide, fluidic pathway subsystem external to the slide, etc.) and/or the flow parameters (e.g., flow rate, flow volume, flow duration, etc.) of one or more fluids (e.g., buffers, air, oil, etc.) through the fluidic pathway subsystem. In a first variation, the fluidic pathway subsystem is configured to transfer fluid from a fluid manifold to a region above the set of wells. In a specific example, a fluidic pathway configured to dispense a partition fluid (e.g., air, oil, buffer, water, etc.) has a diameter of similar size as a space above the walls of the set of wells. Additionally, the fluidic pathway can define an inlet above the set of wells such that the partition fluid is dispensed in a laminar flow above the set of wells. In a second variation, the flow rates of the partition fluids (e.g., air, oil, etc.) are configured to fill a space above the set of wells (e.g., during at least a majority of the duration of the dispensing of the partition fluids, for greater than 80% of the time at which a partition fluid is dispensed, etc.). Additionally or alternatively, S600 can be enabled by any or all of: partition fluid properties (e.g., density, viscosity, etc.), temperature, or any other suitable properties.

In variations (e.g., as shown in FIGS. 6E-6G, where FIG. 6G also describes and depicts aspects of cell lysis within partitioned wells), Block S260 includes dispensing air (shown in FIG. 6E), which functions to remove excess lysis buffer (e.g., remaining from Block S250) and partition the wells from each other, followed by dispensing oil (shown in FIG. 6F), which functions to prevent evaporation of liquid or other content from the set of wells or to prevent diffusion of molecules from one microwell to another microwell. In alternative variations, only air is dispensed, only oil is dispensed, or any other fluid or combination of fluids is dispensed.

As shown in FIGS. 4 and 5E, the method 200 can include providing a lysis environment for the set of cells S270, which functions to release target cell material (e.g., mRNA) from the cells. In relation to Block S270, for each well, at least a subset of target cell material then binds to the probes (e.g., oligonucleotide fragments) of the particle initially co-captured with the cell in the well. The binding of the target cell material to the probes is preferably achieved through poly(A) present on the target cell material (e.g., mRNA), and poly(T) present on the particles. However, binding of target content to probes of the particle can additionally or alternatively be achieved through any other suitable reaction or process.

Block S270 is preferably performed while a barrier (e.g., oil) as described in relation to Block S260 is maintained, which precludes the cell material from moving or leaking from the source well, and into an adjacent well. In some variations, a partition fluid velocity and/or partition fluid barrier are critical in the enablement of this. Additionally or alternatively, a predetermined cocktail of lysis buffer can be critical to maintaining a binding time or other binding conditions. In a specific example, the method includes waiting a predetermined duration of time (e.g., between 15 and 30 minutes, less than 15 minutes, greater than 30 minutes, etc.) for lysis and binding of target cell material (e.g., mRNA) to the set of particles.

The temperature at which the cells are lysed is preferably between 20 and 30 degrees Celsius (e.g., room temperature, between 20 and 25 degrees Celsius, 26 degrees Celsius, etc.). As such, in relation to FIG. 6G, Block S270' can include transmission of heat into the array of wells to facilitate lysis with retention of content within the array of wells. Alternatively, the cells can be lysed at a temperature less than 20 degrees Celsius, greater than 30 degrees Celsius, or any other suitable temperature.

In a first variation, the cells are lysed at room temperature for between 15 and 30 minutes. In a specific example, the cells are lysed at 26 degrees Celsius for 25 minutes. In another variation, cells may be lysed at a temperature of 40 degree Celsius or at 50 degree Celsius.

2.4 Method—Additional Steps

As shown in FIG. 4, the method 200 can optionally include ramping the temperature down and soaking S280, which can function to prevent any unbound target cell material from migrating out (e.g., through evaporation, through diffusion, etc.) of the set of wells. This temperature is preferably between 0 and 5 degrees Celsius, and the soak time is preferably between 5 and 20 minutes. In a specific example, Block S280 includes ramping the temperature down to 2 degrees Celsius and holding for 11 minutes. Additionally or alternatively, S800 can include any other suitable processes at any suitable parameters.

As shown in FIG. 4, the method 200 can optionally include washing away unbound material S290, which functions to remove unbound target cell material (e.g., unbound mRNA) post-lysis. The slide temperature during S900 is preferably maintained at room temperature, but can additionally or alternatively be maintained at another suitable temperature, variable, room temperature, or any other suitable temperature(s). S900 preferably includes flowing in a wash buffer (e.g., through any or all of the fluidic pathways as used in previous steps). The wash buffer can include a detergent, preferably PBS with an RNAase inhibitor (e.g., PBS with 1% IGEPAL). Additionally or alternatively, any other liquids or materials can be used to wash off unbound material. The wash flow rate is preferably configured such that floating target cell material from the wells is pumped to a waste reservoir without having the opportunity to diffuse into neighboring wells. This flow rate, in one variation, is between 50 and 1000 microliters per second. In an embodiment, washing unbound material can comprise flowing a wash buffer configured to remove unbound RNA over the array of wells at a flow rate more than 50 microliters/second, after hybridization of mRNA material to the set of particles.

Block S290 can optionally include removing the wash buffer, which is preferably performed through flowing in air (e.g., air wash). Block S290 can additionally or alternatively include washing the wells with wash beads, wherein the wash beads bind to migrant target cell material (e.g., floating above the set of wells, within the set of wells, etc.). The set of wash beads are preferably magnetic (e.g., oligo d(T) magnetic beads, oligo (dT) magnetic beads, etc.), but can additionally or alternatively be non-magnetic, configured to bind to any suitable probe, or otherwise configured. As such, the wash beads can be of a composition that facilitates retrieval of the wash beads, with bound unwanted or leaked material, from the system.

The washing process is preferably performed multiple times (e.g., twice, three times, between 1 and 10 times, etc.), but can alternatively be performed once, or the method can be performed in the absence of washing.

In a first variation, Block S290 includes washing the slide with a wash buffer absent of wash beads. In a second variation, S900 includes washing the slide with a set of magnetic wash beads. In a first specific example, one-micron magnetic oligo d(T) beads are used. In a second specific example, eight-micron magnetic oligo d(T) beads are used. In another variation, the wash buffer may contain oligo dT fragments containing a non-extensible base. These oligo dT fragments bind to any unbound target mRNA molecules egressing or remaining in the microwells but after binding unable to get converted to CDNA during downstream reverse transcription because of the presence of non-extensible base in around the oligo-dT sequence.

As shown in FIG. 4, the method can optionally include any processing of the cells S299. The cells can be processed within wells, outside of wells (e.g., after individual cells have been extracted, after all cells have been extracted, etc.), or at any other suitable location or combination of locations.

Figure 5F:
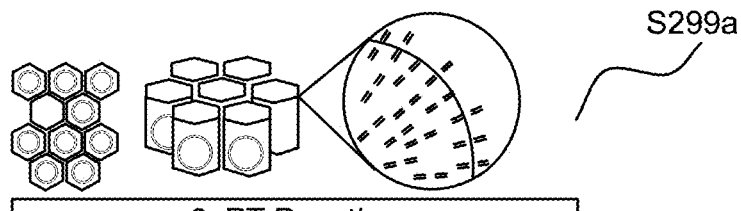

In one variation, Block S299 includes a first operation including an on-chip reverse transcriptase process, depicted as S299a in FIG. 5F. In a first example, this is performed at a temperature of 58° C., and for a duration of time of 16 minutes. In another variation, the on-chip reverse transcriptase process is performed immediately after the lysis of cells while being partitioned in its microwells. For this process, the reverse transcription reagents are optimized and co-delivered with the lysis buffer cocktail.

Figure 5G:
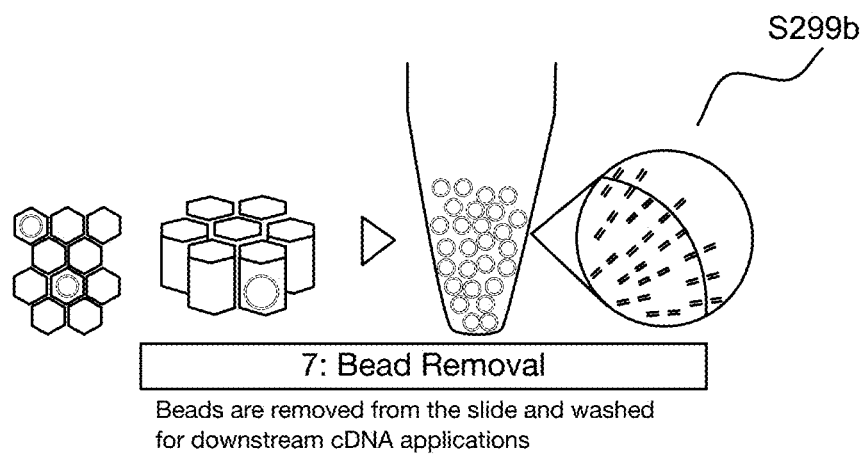

Block S299 can also include removing the set of particles bound to target cell material and proceeding to a set of steps to prepare the material for DNA sequencing, depicted as S299b in FIG. 5G. In an example, this includes extracting the set of particles from the array of wells (e.g., using an aspiration process, using a pressure-driven process, using a magnetic retrieval process, using a gravity or centrifugal force-associated process, etc.) and separating them from any remaining wash beads (e.g., prior to removing first set of beads, after removing first set of beads, etc.).

Figure 5H:
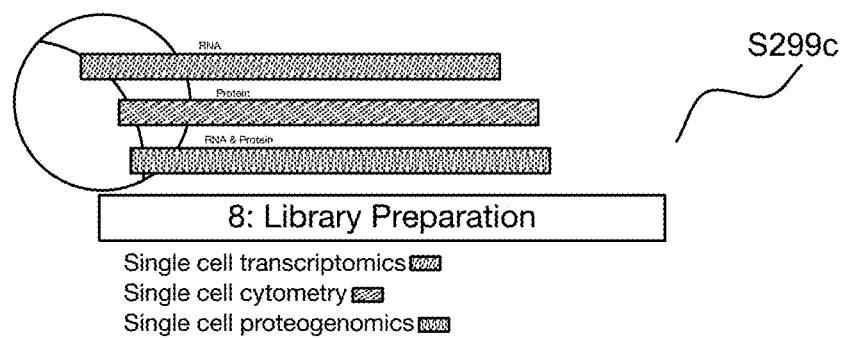

Block S299 can additionally or alternatively any other suitable processing and analysis steps. This can include any or all of future processing of cells (e.g., through reverse transcription), polymerase chain reaction sequencing (e.g., single cell genome, DNA/RNA sequencing, library prep, depicted as S299c in FIG. 5H, etc.), data analysis, or any other suitable processes.

Figure 7A:
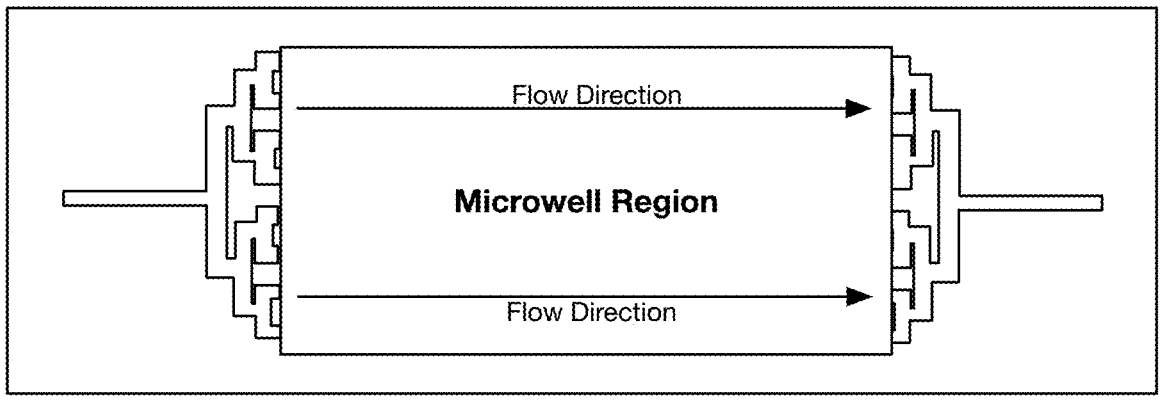
FIGS. 7A-7B depict variations of system and method configurations for single cell capture and processing, with leakage control.
Figure 7B:
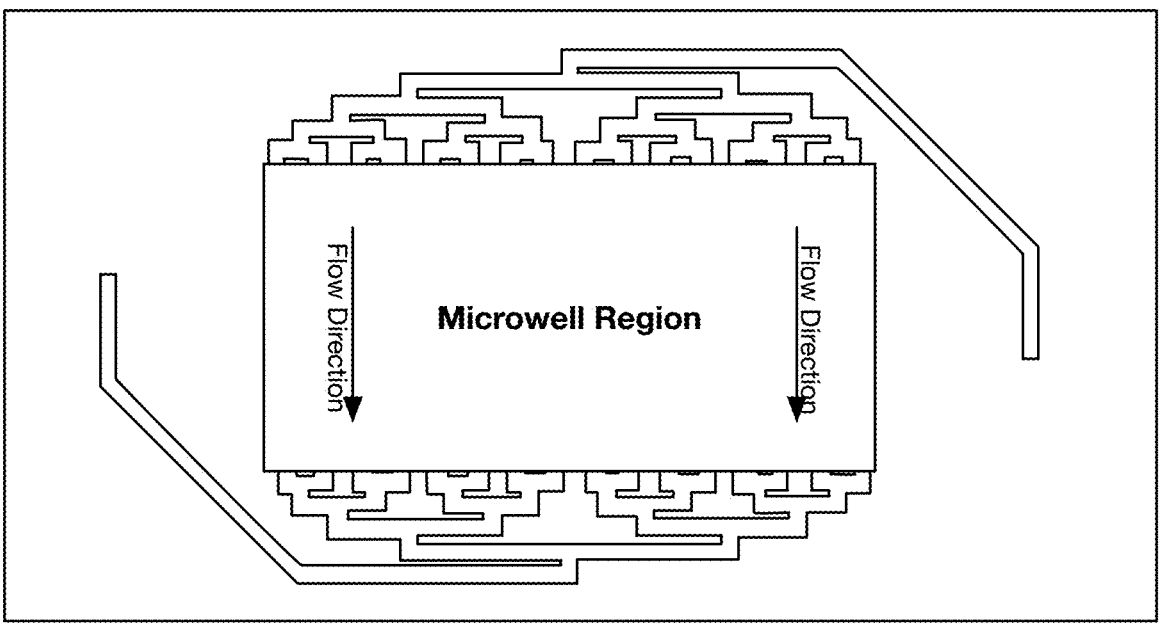

In relation to system configurations for further preventing leakage, FIGS. 7A-7B depict example fluid network configurations and flow directions across a substrate associated with prevention of leakage of contents of a well to adjacent wells. FIG. 7A depicts a first configuration where the substrate for the array of wells includes a short axis, a long axis, and a network of fluid channels defining one or more flow paths preferentially aligned with the long axis and coupled to the cavity in fluid communication with the microwell region. The configuration shown in FIG. 7A can contribute to higher risk of leakage of well contents, due to a configuration of longer distances for fluid travel across the array of wells. FIG. 7B alternatively depicts a second configuration where the substrate for the array of wells includes a short axis, a long axis, and a network of fluid channels defining one or more flow paths preferentially aligned with the short axis and coupled to the cavity in fluid communication with the microwell region. The configuration shown in FIG. 7B can contribute to lower risk of leakage of well contents, due to a configuration of shorter distances for fluid travel across the array of wells. As such, in relation to Blocks S230, S250, S260, S270, and S290 described above, the method 200 can include receiving one or more of the wash buffer, the lysis buffer, and the partitioning fluid into the network of fluid channels along a shorter distance of travel due to the configuration of fluid channels in communication with the array of microwells.

2.5 Method—Example

In one example, the method 200 includes capturing cells in a set of microwells; capturing 20-micron particles (e.g., HDBB) in the set of microwells; washing off excess particles; soaking the microwells at four degrees Celsius for 11 minutes; flowing in cold (e.g., four degrees Celsius) lysis buffer for no more than 30 seconds; partitioning the wells using air followed by oil; lysing the cells at room temperature for 25 minutes; ramping the temperature down to two degrees Celsius and soaking the contents of the wells for 11 minutes; flowing in wash buffer (e.g., PBS with RNAase inhibitor); removing the first wash buffer using air wash; flowing in the wash buffer for a second time; removing the wash buffer using air wash; performing on-chip reverse transcriptase at 58 degrees Celsius for 16 minutes; removing the particles from the slide and proceeding to sequencing and data analysis. However, variations of the example can be performed in any other suitable manner.

Additionally or alternatively, the method 200 can include any other suitable processes performed in any suitable order.

The FIGURES illustrate the architecture, functionality and operation of possible implementations of systems, methods and computer program products according to preferred embodiments, example configurations, and variations thereof. In this regard, each block in the flowchart or block diagrams may represent a module, segment, or portion of code, which comprises one or more executable instructions for implementing the specified logical function(s). It should also be noted that, in some alternative implementations, the functions noted in the block can occur out of the order noted in the FIGURES. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

As a person skilled in the art will recognize from the previous detailed description and from the figures and claims, modifications and changes can be made to the preferred embodiments of the invention without departing from the scope of this invention defined in the following claims.

What is claimed is:

1. A method comprising:
   receiving, in single-cell format, a set of target cells into an array of wells defined at a surface plane of a substrate, wherein each well in the array of wells extends perpendicular to and into the surface plane into the substrate;
   receiving a set of particles into the array of wells, thereby co-capturing the set of target cells and the set of particles across the array of wells, wherein receiving the set of particles and the set of target cells comprises retaining the set of particles closer to the surface plane than the set of target cells;
   achieving a state of specific capture for the array of wells, wherein a well of the array of wells in the state of specific capture has a target cell of the set of target cells and a particle of the set of particles and a width configured to prevent positioning of the target cell of the set of target cells laterally adjacent to the particle of the set of particles, upon receiving a washing fluid into a cavity in communication with the array of wells and transmitting excess particles of the set of particles away from the array of wells;
   providing a lysis environment for the set of cells upon receiving a lysis buffer into the cavity;

partitioning each of the array of wells from adjacent wells of the array of wells, at the surface plane, upon displacing the lysis buffer from the cavity with a gas volume;

preventing evaporation of contents of the array of wells upon receiving a partitioning fluid into the cavity; and retaining intercellular material of the set of target cells, within the array of wells, with transmission of heat into the array of wells.

2. The method of claim 1, wherein the substrate comprises: a short axis, a long axis, and a network of fluid channels defining one or more flow paths preferentially aligned with the short axis and coupled to the cavity, wherein receiving one or more of the lysis buffer and the partitioning fluid comprises receiving one or more of the lysis buffer and the partitioning fluid into the network of fluid channels.

3. The method of claim 1, wherein receiving the lysis buffer comprises receiving the lysis buffer at a temperature between 1° C. and 15° C.

4. The method of claim 3, wherein receiving the lysis buffer comprises retaining the lysis buffer within the cavity for a residence duration below 40 seconds.

5. The method of claim 1, wherein retaining intracellular material comprises retaining mRNA material, of the set of target cells, hybridized to the set of particles individually within the array of wells.

6. The method of claim 1, wherein each of the set of particles comprises a polystyrene coating and a unique biopolymer composite barcode.

7. The method of claim 1, wherein receiving the set of cells comprises receiving the set of cells at a first concentration configured for less than 50% occupancy of the array of wells, thereby promoting capture of the set of cells in single-cell format, and wherein receiving the set of particles comprises receiving the set of particles at a second concentration higher than the first concentration.

8. The method of claim 1, wherein a cross-section of each well in the array of wells defines a polygon, and wherein each well in the array of wells comprises a depth greater than a sum of a particle diameter of the set of particles and a cell diameter of the set of target cells.

9. The method of claim 1, wherein the partitioning fluid comprises an oil.

10. A method comprising:
receiving, in single-cell format, a set of target cells into an array of wells defined at a surface plane of a substrate;

receiving a set of particles into the array of wells, thereby co-capturing the set of target cells and the set of particles across the array of wells, wherein receiving the set of particles and the set of target cells comprises retaining the set of particles closer to the surface plane than the set of target cells;

achieving a state of specific capture for the array of wells, wherein a well of the array of wells in the state of specific capture has a target cell of the set of target cells and a particle of the set of particles, upon receiving a washing fluid into a cavity in communication with the array of wells and transmitting excess particles of the set of particles away from the array of wells;

providing a lysis environment for the set of cells upon receiving a lysis buffer into the cavity;

receiving a partitioning fluid into the cavity, thereby displacing the lysis buffer from the cavity and partitioning each of the array of wells from adjacent wells of the array of wells, at the surface plane; and retaining intercellular material of the set of target cells, individually with the set of particles within the array of wells, thereby mitigating leakage of intracellular material of a first well to a second well of the array of wells.

11. The method of claim 10, wherein the substrate comprises: a network of fluid channels defining one or more flow paths preferentially aligned with a short axis of the substrate and coupled to the cavity, wherein receiving one or more of the lysis buffer and the partitioning fluid comprises receiving one or more of the lysis buffer and the partitioning fluid into the network of fluid channels.

12. The method of claim 10, wherein receiving at least one of the set of target cells, the set of particles, the washing fluid, the lysis buffer, and the partitioning fluid comprises receiving with a laminar flow process.

13. The method of claim 10, wherein the partitioning fluid comprises at least one of air and an oil.

14. The method of claim 10, wherein receiving the lysis buffer comprises receiving the lysis buffer at a temperature between 1° C. and 15° C.

15. The method of claim 10, wherein the lysis buffer is pre-cooled below 15° C. prior to entering the cavity over the array of wells.

16. The method of claim 10, wherein receiving the lysis buffer comprises retaining the lysis buffer within the cavity for a residence duration below 40 seconds.

17. The method of claim 10, wherein retaining intracellular material comprises transmitting heat through the substrate and into the array of wells, producing a well temperature within the array of wells between 15° C. and 35° C.

18. The method of claim 10, wherein retaining intracellular material comprises retaining mRNA material, of the set of target cells, hybridized to oligonucleotide probes coupled to the set of particles, individually within the array of wells.

19. The method of claim 10, further comprising flowing a wash buffer configured to remove unbound RNA over the array of wells at a flow rate more than 50 microliters/second, after hybridization of mRNA material to the set of particles.

20. The method of claim 18, further comprising performing a reverse transcription process with retained mRNA material within the array of wells.

* * * * *